(12) United States Patent
Balberg et al.

(10) Patent No.: US 8,108,022 B2
(45) Date of Patent: *Jan. 31, 2012

(54) METHOD AND APPARATUS FOR NONINVASIVELY MONITORING PARAMETERS OF A REGION OF INTEREST IN A HUMAN BODY

(75) Inventors: Michal Balberg, Jerusalem (IL); Revital Pery-Schechter, Rishon Lezion (IL); Michal Olshansky, Tel Aviv (IL)

(73) Assignee: OR-NIM Medical Ltd., Tel Aviv (IL)

( * ) Notice: Subject to any disclaimer, the term of this patent is extended or adjusted under 35 U.S.C. 154(b) by 1789 days.

This patent is subject to a terminal disclaimer.

(21) Appl. No.: 11/327,381

(22) Filed: Jan. 9, 2006

(65) Prior Publication Data

US 2006/0122475 A1 Jun. 8, 2006

Related U.S. Application Data

(63) Continuation of application No. 10/545,798, filed as application No. PCT/IL2004/00835 on Sep. 12, 2004.

(60) Provisional application No. 60/502,212, filed on Sep. 12, 2003, provisional application No. 60/502,210, filed on Sep. 12, 2003, provisional application No. 60/553,142, filed on Mar. 16, 2004, provisional application No. 60/581,376, filed on Jun. 22, 2004.

(51) Int. Cl.
*A61B 5/1455* (2006.01)
*A61B 6/00* (2006.01)
(52) U.S. Cl. ...................................... 600/310; 600/407
(58) Field of Classification Search ........... 600/309–344
See application file for complete search history.

(56) References Cited

U.S. PATENT DOCUMENTS 4,653,498 A 3/1987 New, Jr. et al.
(Continued)

FOREIGN PATENT DOCUMENTS

DE 19654053 A1 6/1998
(Continued)

OTHER PUBLICATIONS

A. Zourabian et al "Trans-abdominal monitoring of fetal arterial blood oxygenation using pulse oxymetry" Journal of Biomedical Optics, vol. 5, No. 4, (Oct. 2000) pp. 391-405.
Keinle et al "In vivo determination of the optical properties of muscle with time-resolved reflectance using a layered model" Physics in Medicine and Biology (1999) vol. 44 pp. 2689-2702.
(Continued)

*Primary Examiner* — Eric Winakur
*Assistant Examiner* — Marjan Fardanesh
(74) *Attorney, Agent, or Firm* — Browdy and Neimark, PLLC

(57) ABSTRACT

Apparatus and methods including a probe device for monitoring a parameter of a region of interest in a human body. A support structure of the device carries an arrangement of light output ports of a light source assembly, light input ports of a light detection assembly, and an acoustic output port of an acoustic unit. The arrangement is such as to enable selection of a light output port, a light input port, and an acoustic output port for an operating condition at which, acoustic waves from the acoustic output port and illuminating light from the light output port overlap in a region within the region of interest in the body thereby inducing tagging of light by the acoustic waves, and the light input port collects light scattered from the overlapping region and light scattered from outside the region of interest. Other embodiments are also described.

30 Claims, 11 Drawing Sheets

U.S. PATENT DOCUMENTS

| | | | |
|---|---|---|---|
| 5,193,543 | A | 3/1993 | Yelderman |
| 5,293,873 | A | 3/1994 | Fang |
| 5,494,032 | A | 2/1996 | Robinson et al. |
| 6,002,958 | A | 12/1999 | Godik |
| 6,041,248 | A | 3/2000 | Wang |
| 6,240,309 | B1 * | 5/2001 | Yamashita et al. ............ 600/407 |
| 6,264,610 | B1 | 7/2001 | Zhu |
| 6,738,653 | B1 * | 5/2004 | Sfez et al. ..................... 600/322 |
| 6,815,694 | B2 | 11/2004 | Sfez et al. |
| 7,747,301 | B2 * | 6/2010 | Cheng et al. .................. 600/322 |

FOREIGN PATENT DOCUMENTS

| | | |
|---|---|---|
| EP | 0549835 A1 | 7/1993 |
| EP | 1008326 A2 | 6/2000 |
| WO | 98/50781 A1 | 11/1998 |
| WO | WO9850781 | 11/1998 |
| WO | 02/08740 A2 | 1/2002 |

OTHER PUBLICATIONS

Leveque-Fort et al "In situ local tissue characterization and imaging by backscattering acousto-optic imaging" Optics Communications vol. 196 (2001) pp. 127-131.

Lev A and B.G. Sfex "Direct, noninvasive detection of photon density in turbid media" Optics Letters (2002) vol. 27, No. 7, pp. 473-475.

F. Rousseau, et al "Robust and Automatic Calibration Method for 3D Freehand Ultrasound", Medical Image Computing and Computer Assisted Intervention, MICCAI'03, (Nov. 2003).

An Office Action dated Jan. 27, 2011, which issued during the prosecution of Applicant's European Patent Application No. 05 718 873. 2.

An Office Action dated Apr. 13, 2011, which issued during the prosecution of Applicant's U.S. Appl. No. 10/545,798.

* cited by examiner

METHOD AND APPARATUS FOR NONINVASIVELY MONITORING PARAMETERS OF A REGION OF INTEREST IN A HUMAN BODY

The present application is a Continuation of PCT/IL04/00835 filed Sep. 12, 2003, now Ser. No. 10/545,798.

FIELD OF THE INVENTION

This invention relates to a method and apparatus for noninvasive monitoring of parameters of a region of interest in a human body, such as oxygen saturation and/or concentration of analyte(s) in blood.

BACKGROUND OF THE INVENTION

Monitoring of the well-being of the fetus inside the uterus is very important and is carried periodically with respect to various parameters of the fetus. One of the important parameters to be monitored is oxygen saturation. Various techniques have been developed to enable noninvasive measurements of oxygen saturation.

For example, U.S. Pat. No. 5,494,032 discloses an oximeter for reliable clinical determination of blood oxygen saturation in a fetus. This technique utilizes a multiple frequency light source which is coupled to an optical fiber. The output of the fiber is used to illuminate blood containing tissue of the fetus. The reflected light is transmitted back to the apparatus where the light intensities are simultaneously detected at multiple frequencies. The resulting spectrum is then analyzed for determination of oxygen saturation. The analysis method uses multivariate calibration techniques that compensate for nonlinear spectral response, model interfering spectral responses and detect outlier data with high sensitivity.

A pulse oximetry based technique for determining the fetal arterial blood oxygenation is disclosed in the following article: A. Zourabian et al., "Trans-abdominal monitoring of fetal arterial blood oxygenation using pulse oximetry", Journal of Biomedical Optics, Vol. 5, No. 4, October 2000, pp. 391-405.

U.S. Pat. No. 6,041,248 describes a method and apparatus for frequency encoded ultrasound-modulated optical tomography of dense turbid media. The apparatus includes a function generator producing a frequency sweep signal which is applied to an ultrasonic transducer. The ultrasonic transducer produces ultrasonic wave in a turbid medium. Coherent light from a laser is passed through turbid medium where it is modulated by the ultrasonic wave. A photomultiplier tube detects the light which passes through the turbid medium. The signal from the photomultiplier tube is fed to an oscilloscope and then to a computer where differences in light intensity at different frequencies can determine the location of objects in the turbid medium.

The conventionally used techniques for monitoring the well-being of the fetus inside the uterus utilize measuring the fetal-heart-rate (FHR) by placing sensors on the skin of the mother's abdomen proximal to the fetus. These sensors transmit acoustic waves and provide data indicative of the Doppler shift of an acoustic wave reflected from the fetal heart, enabling calculation of the heart rate based on this shift. A normal fetal-heart-rate (FHR) pattern is usually associated with the delivery of a normal well-oxygenated infant. However, a non-reassuring FHR is not always associated with the delivery of a compromised infant.

In the case of non-reassuring FHR, the fetal blood oxygen saturation level can be measured only post membrane rupture by either fetal scalp sampling, which measures the pH level of the fetal blood, or by attaching a pulse oximeter to the presenting part of the fetal head during labor. Both of these methods are performed following the rupture of membranes where the fetal scalp and/or cheeks can be reached.

Another important procedure to be done to monitor the well-being of the fetus consists of assessing the maturity of fetal lungs, which is one of the major concerns of pre-term deliveries. If the baby is delivered and the lungs are not mature, the baby may develop Respiratory Distress Syndrome (RDS), which can result either in fetal death or in long-lasting periods of repeated respiratory difficulty.

In cases where intervention is considered in the course of pregnancy (such as caesarean section or induction of labor) and there is a need to assess the maturity of the lungs, amniotic fluid is drained. Measuring phospholipids in amniotic fluid as the lecithin/sphingomyelin ratio using the thin-layer chromatography method has been the established clinical procedure for predicting fetal lung maturity. Although it is the clinical "gold standard" method, it remains a time-consuming process, has a large intralaboratory and interlaboratory coefficient of variation, and requires expertise. In addition, the procedure of amniotic fluid drainage itself is invasive and suffers a small risk of abortion. Additional techniques that are used for assessing lung maturity levels include measuring the number of lamellar bodies in a volume of amniotic fluid, measuring the prostaglandin level in amniotic fluid and measuring the fluorescence polarization of a sampled amniotic fluid.

When a fetus is acutely distressed, for example as a result of strangulation by the umbilical cord, the bowel content, meconium, may be passed into the amniotic fluid (AF). Assessment of meconial contamination of AF is important in the management of late pregnancy. It appears in nearly one third of all fetuses by 42 weeks of gestation. In cases where the fetus gasps during delivery, inhaling the sticky meconium into the upper respiratory tract results in partial airways obstruction. Meconium aspiration syndrome occurs in 0.2% to 1% of all deliveries and has a mortality rate as high as 18%. The disease is responsible for 2% of all prenatal deaths.

To date, meconium stained amniotic fluid is diagnosed following the rupture of membranes, when the amniotic fluid is drained. However, in cases where the fetus head is tightly fitted in the pelvis, the amniotic fluid is not drained out resulting in misdiagnosis of the potential harmful outcome to the respiratory tract.

SUMMARY OF THE INVENTION

There is accordingly a need in the art to facilitate noninvasive monitoring of parameters of a region of interest in a human body, by providing a novel noninvasive method and apparatus.

The technique of the present invention provides for monitoring blood and/or tissue parameters and/or parameters of fluids of a region of interest in a human body, for example the concentration of an analyte in blood, fluid reservoirs or tissue regions in a human body; as well as fetus condition in utero (e.g., the fetal oxygen saturation level as well as the concentration of analyte in fetal blood; and the maturity of fetal lungs and the presence of meconium, prior to membrane rupture).

It should be understood that the term "region of interest" signifies a tissues region or a fluid contained in a reservoir or cavity inside a body. The region of interest may be a fetus region (e.g., fetus head), amniotic fluid, vicinity of blood vessels, etc. The term "fetus-related region of interest" used herein signifies either one of fetus and amniotic fluid regions.

The main idea of the present invention consists of non-invasively monitoring the optical properties of a region of interest in a human (or animal) body utilizing the principles of ultrasound tagging of light, which in the present invention is aimed at distinguishing between optical responses of the region of interest in the selected volume (e.g., fetus, amniotic fluid, blood vessel) and the surroundings outside the region of interest; and/or significantly improving pulse oximetry based measurements.

According to one aspect of the present invention, a body portion (e.g., the abdomen of a pregnant woman) containing a region of interest (fetus) is irradiated with light (e.g., of at least two different wavelengths) and is irradiated with acoustic waves, in a manner to ensure optimal operating condition for measurements. This operating condition is such that the illuminating light and acoustic waves overlap within the region of interest and thus light scattered from the region of interest is "tagged" by acoustic waves (i.e., the frequency of light is modulated by the frequency of the acoustic waves) while substantially do not overlap in a region outside the region of interest, and to ensure that detected light includes a portion of light scattered by the region of interest and tagged by acoustic waves and a portion of untagged light scattered by the region outside the region of interest. This allows for distinguishing between light responses of the region of interest and its surroundings (e.g., fetus and maternal tissues). It should be understood that the term "acoustic wave" refer to acoustic radiation of either one of the following type: continuous wave, pulses, bursts.

It should be understood that for the purposes of the present invention the term "maternal tissues" used herein refers to all the tissues within a region surrounding the fetus-related region of interest (fetus itself or amniotic fluid containing the fetus). Considering the region of interest is fetus, the term "maternal tissues" refers to maternal tissues, amniotic fluid, and uterine wall.

According to another aspect of the present invention, the above operating condition is used in pulse oximetry measurements for determining oxygen saturation level in a region of interest (in mammalian blood and/or blood vessels). Measured data that needs to be analyzed is, for example, in the form of a power spectrum of ultrasound-tagged light response of the region of interest, which is practically insensitive to minor movements of regions outside the region of interest, while pure pulse oximetric measurements are highly sensitive to such movements.

Preferably, the present invention in either of its aspects utilizes obtaining of measured data in the form of time dependent and/or wavelength dependent variations of ultrasound-tagged light signals for at least two wavelengths of illuminating light.

The present invention provides for non-invasively determining such parameters as oxygen saturation level in the region of interest (e.g., fetus, blood vessel), concentration of a substance or a structure within the region of interest (e.g., fetus, amniotic fluid), the presence and concentration of lamellar bodies in amniotic fluid for determining the level of lung maturity of the fetus, the presence and/or concentration of meconium in the amniotic fluid, presence and/or concentration of blood in the amniotic fluid; as well as for noninvasive monitoring the optical properties of other extravascular fluids such as pleural, pericardial, peritoneal (around the abdominal and pelvis cavities) and synovial fluids. It is important to note that according to the invention, acoustic (ultrasound) radiation used for measurements needs not be focused, since the measurements utilize ultrasound tagging solely for the purposes of distinguishing between light responses of the region of interest and its surroundings, and/or for increasing signal to noise ratio of ultrasound tagging based measurements.

The present invention utilizes the principles of oximetry for processing the measured data. Accordingly, the illumination with at least two different wavelengths is applied. Preferably, the light response signals are collected over a time period larger than a heart beat, and the principles of pulse oximetry are used to determine the oxygen saturation.

Preferably, a measurement unit (an illumination assembly, a light detection assembly, and an ultrasound transducer arrangement) is placed in close contact with the respective body portion (e.g., maternal tissues being in contact with amniotic sac containing a fetus). As indicated above, the illumination assembly is configured and operable to illuminate the body portion with at least two wavelengths. The ultrasound transducer arrangement is configured and operable to transmit acoustic waves into the same volume from which the light detector collects scattered light.

The light detection assembly may be oriented for collecting both back scattered light and forward scattered light.

Preferably, the present invention utilizes ultrasound imaging, carried out prior to measurements and aimed at determining optimal positioning of the illumination assembly, light detection assembly and acoustic waves propagation to thereby provide the operating condition for measurements. The ultrasound imaging may and may not utilize the same ultrasound transducer arrangement that is used for measurements. Preferably, the invention also provides for using ultrasound radiation for determining such parameters of blood in the region of interest (e.g., fetus) as blood flow, tissue velocity profile, etc. To this end, reflections of ultrasound radiation from the irradiated region are analyzed using any known suitable Doppler-based techniques. The incident ultrasound radiation may be in the form of continuous waves or pulses (gates).

According to an embodiment of the present invention maternal oxygen saturation level is detected using the same apparatus being used to measure fetal oxygen saturation level.

The present invention can be used for measuring in more than one fetus presented inside the uterus. In this case, the oxygen saturation level (or other fetal parameters) of each fetus is measured independently using the same apparatus; or several different apparatuses, one for each fetus, all associated with the same control unit (data processing and analyzing utility). Each fetus is located using an ultrasound imaging system, and the optimal arrangement of the light sources, detectors and ultrasound transducers is determined for monitoring the oxygen saturation level of each fetus.

There is thus provided according to one aspect of the invention a monitoring system for use in non-invasively monitoring at least one parameter of a region of interest in a human body, the system comprising:

a measurement unit comprising an optical unit having an illumination assembly configured to define at least one output port for illuminating light, and a light detection assembly configured to define at least one light input port for collecting light scattered from the illuminated body portion and to generate measured data indicative of the collected light; and an acoustic unit configured to generate acoustic waves of a predetermined ultrasound frequency range; the measurement unit being configured and operable to provide an operating condition such that the acoustic waves of the predetermined frequency range overlap with an illuminating region within the region of interest and substantially do not overlap with a region outside the region of interest, and that the detection assembly collects light scattered from the region of interest and light scattered from the region outside the region of interest, the measured data being thereby indicative of scattered light having both ultrasound tagged and untagged light portions, thereby enabling to distinguish between light responses of the region of interest and the region outside the region of interest;

a control unit, which is connectable to the optical unit and to the acoustic unit to operate these units, the control unit being responsive to the measured data and preprogrammed to process and analyze the measured data to extract therefrom a data portion associated with the light response of the region of interest and determine said at least one parameter of the region of interest.

According to another aspect of the invention, there is provided a monitoring system for use in non-invasively monitoring at least one parameter of a region of interest in a human body, the system comprising:

a measurement unit comprising an optical unit configured for generating illuminating light and for collecting light and generating measured data indicative of the collected light; and an acoustic unit configured to generate unfocused acoustic waves of a predetermined ultrasound frequency range; the measurement unit being configured and operable to provide an operating condition such that the acoustic waves of the predetermined frequency range overlap with an illuminating region within the region of interest while substantially not overlapping within a region outside the region of interest, and that the detection assembly collects light scattered from the region of interest and light scattered from the region outside the region of interest, the measured data being thereby indicative of scattered light having both ultrasound tagged and untagged light portions, thereby enabling to distinguish between light responses of the region of interest and the region outside the region of interest;

a control unit, which is connectable to the optical unit and to the acoustic unit to operate these units, the control unit being responsive to the measured data and preprogrammed to process and analyze the measured data to extract therefrom a data portion associated with the light response of the region of interest and determine said at least one parameter of the region of interest.

According to yet another aspect of the invention, there is provided a system for use in noninvasive monitoring at least one parameter of a region of interest in a human body, the system comprising:

a measurement unit comprising an optical unit having an illumination assembly configured to define at least one output port for illuminating light, and a light detection assembly configured to define at least one light input port for collecting light and to generate measured data indicative of the collected light; and an acoustic unit configured to generate acoustic waves of a predetermined ultrasound frequency range;

a control unit, which is connectable to the optical unit and to the acoustic unit to operate these units, the control unit being responsive to the measured data and preprogrammed to process and analyze the measured data to extract therefrom data indicative of a light response of the region of interest and determine the at least one desired parameter, the control unit being operable to provide optimal positioning of the optical unit and the acoustic unit to satisfy an operating condition for measurements, said operating condition being such that acoustic waves of the predetermined frequency range and illuminating light overlap within the region of interest and substantially do not overlap in a region outside the region of interest, and in that the detection assembly collects the light scattered from the region of interest and light scattered from the region outside the region of interest; the measured data being thereby indicative of scattered light having both ultrasound tagged and untagged light portions, thereby enabling to analyze the measured data to extract therefrom a data portion associated with the light response of the region of interest and determine said at least one parameter of the region of interest.

According to yet another aspect of the invention, there is provided a probe device for use in a system for monitoring at least one parameter of a region of interest in a human body, the probe comprising: a support structure configured to contact a body portion, said support structure carrying an array of at least two light output ports arranged in a spaced-apart relationship and being optically coupled to a light source assembly, an array of light input ports arranged in a spaced-apart relationship and being optically coupled to a light detection assembly, and at least one acoustic output port of an acoustic unit, the arrangement of the light ports and the acoustic unit being such as to allow selection of at least one of said light output ports, at least one of the light input ports and at least one of the acoustic output ports such that acoustic waves of a predetermined frequency range coming from said at least one selected acoustic output port and illuminating light coming from said at least one selected light output port overlap within a region of interest in the body, and in that said at least one light input port collects light scattered from the overlapping region and light scattered from outside the region of interest.

According to yet another aspect of the invention, there is provided a probe device for use in a system for monitoring at least one parameter of a region of interest in a human body, the probe comprising: a support structure configured to contact a body portion, said support structure carrying at least one light output port optically coupled to a light source assembly, at least two light input ports optically coupled to a light detection assembly, and at least one acoustic output port of an acoustic unit, the arrangement of the light and acoustic ports being such as to allow selection of the light and acoustic ports for measurements such that, with the selected ports, acoustic waves of a predetermined frequency range and illuminating light overlap within a region of interest in the body and that the at least one light input port collects light scattered from the overlapping region and light scattered from outside of the region of interest.

According to yet another aspect of the invention, there is provided a probe device for use in a system for monitoring at least one parameter of a region of interest in a human body, the probe comprising: a support structure configured to contact a body portion, said support structure carrying at least two light output port optically coupled to a light source assembly, at least one light input port optically coupled to a light detection assembly, and at least one acoustic output port of an acoustic unit, the arrangement of the light and acoustic ports being such as to allow selection of the light and acoustic ports for measurements such that, with the selected ports, acoustic waves of a predetermined frequency range and illuminating light overlap within a region of interest in the body and that detected light includes scattered from the overlapping region and light scattered from outside of the region of interest.

According to yet another aspect of the invention, there is provided a method for use in noninvasive monitoring at least one parameter of a region of interest in a human body, the method comprising: operating an optical unit and an acoustic unit so as to provide that ultrasound waves of a predetermined frequency range and illuminating light overlap within the region of interest and substantially do not overlap with a region outside the region of interest, thereby producing measured data indicative of collected light including scattered light having ultrasound tagged and untagged light portions, thereby enabling extraction of a light response of the region of interest from all the other light portions in the collected light.

According to yet another aspect of the invention, there is provided a method for use in noninvasive monitoring oxygen saturation level, the method comprising: applying ultrasound tagging of light in pulse oxymetric measurements, obtaining measured data indicative of time dependent variations of ultrasound tagged light signals scattered from a region of interest as a function of at least one of time and, for at least two different wavelength of illuminating light, and analyzing the measured data to calculate the oxygen saturation level.

According to yet another aspect of the invention, there is provided a method for use in noninvasive monitoring at least one parameter of a region of interest in a human body, the method comprising:
providing an optical unit having an illumination assembly configured to define at least one output port for illuminating light; and a light detection assembly configured to define at least one light input port for collecting light, and to generate measured data indicative of the collected light; and providing an acoustic unit configured to generate acoustic waves of a predetermined ultrasound frequency range;
providing an optimal positioning of the optical and acoustic units with respect to each other and with respect to the region of interest, said optimal positioning satisfying an operating condition resulting in that the ultrasound waves of the predetermined frequency range overlap with the illuminating light within the region of interest, while substantially not overlapping a region outside the region of interest, and in that the detection assembly collects light scattered from the overlapping region and from the region outside the region of interest;
operating the optical and acoustic units, when in the optimal positioning, and generating measured data indicative of collected light including scattered light having ultrasound tagged and untagged light portions, thereby enabling extraction of a light response of the region of interest from all the other light portions in the collected light.

According to yet another aspect of the invention, there is provided method for use in noninvasive monitoring at least one parameter of a fetus-related region of interest, the method comprising:
providing an optical unit having an illumination assembly configured to define at least one output port for the illuminating light; and a light detection assembly configured to define at least one light input port for collecting light, and to generate measured data indicative of the collected light; and providing an acoustic unit configured to generate acoustic waves of a predetermined ultrasound frequency range;
providing an optimal positioning of the optical and acoustic units with respect to each other and with respect to the fetus-related region of interest, said optimal positioning satisfying an operating condition resulting in that the ultrasound waves of the predetermined frequency range overlap with the illuminating light within the fetus-related region of interest, while substantially not overlapping in a maternal tissues region outside the fetus-related region of interest, and in that the detection assembly collects light scattered from the fetus-related region of interest and from the maternal tissues region;
operating the optical and acoustic units, when in the optimal positioning, and generating measured data indicative of collected light including scattered light having ultrasound tagged and untagged light portions, thereby enabling extraction from the measured data a data portion indicative of a light response of the fetus-related region of interest.

According to yet another aspect of the invention, there is provided a method for operating a monitoring system configured for noninvasive monitoring at least one parameter of a region of interest in a human body, which system comprises an optical unit and an acoustic unit configured to generate acoustic waves of a predetermined ultrasound frequency range, the method comprising:
operating the monitoring system to provide an optimal positioning of the optical and acoustic units with respect to each other and with respect to the region of interest to satisfy an operating condition for measurements, said operating condition resulting in that the ultrasound waves of the predetermined frequency range overlap with illuminating light generated by the optical unit within the region of interest, while substantially not overlapping in a region outside the region of interest, and in that a detection assembly of the optical unit collects light scattered from the region of interest and from the region outside the region of interest, thereby obtaining measured data indicative of scattered light having ultrasound tagged and untagged light portions, and enabling extraction from said measured data a data portion indicative of a light response of the region of interest.

The technique of the present invention may be used for noninvasive monitoring of various parameters of human blood and tissue. More specifically, the present invention is useful for monitoring fetal blood conditions and is therefore described below with respect to this application.

BRIEF DESCRIPTION OF THE DRAWINGS

In order to understand the invention and to see how it may be carried out in practice, preferred embodiment will now be described, by way of non-limiting examples only, with reference to the accompanying drawings, in which.

DETAILED DESCRIPTION OF THE INVENTION

Figure 1A:
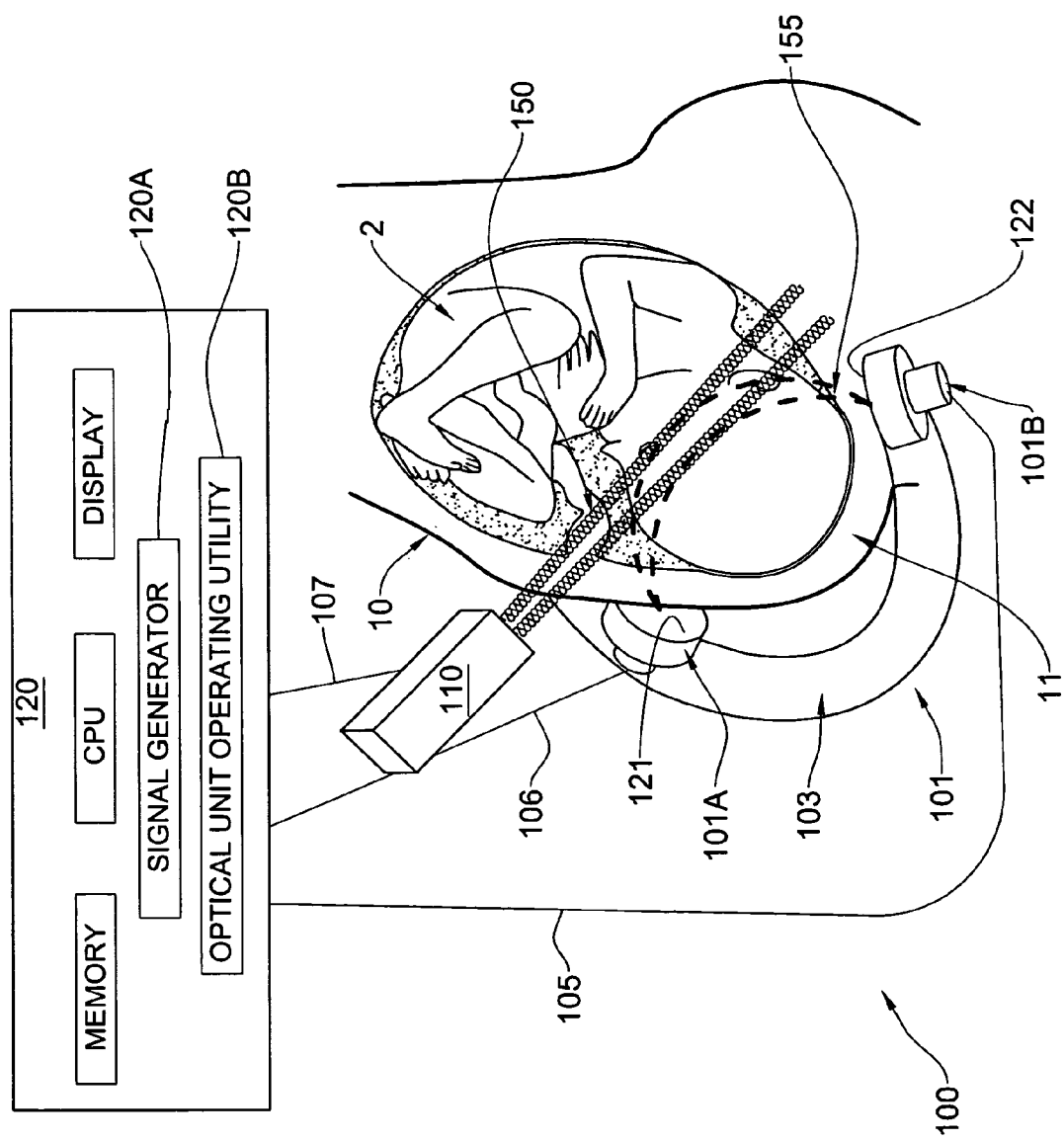
FIG. 1A schematically illustrates a monitoring apparatus according to one embodiment of the invention for monitoring oxygen saturation or a fetus or any other region of interest in a human or animal body.

Referring to FIG. 1A, there is schematically illustrated a monitoring apparatus, generally designated 100, constructed and operated as a fetal oxygen saturation monitor according to the invention. It should, however, be understood that the apparatus configuration is suitable for measuring various other parameters of a fetus 2 (such as the concentration of an analyte in the fetal blood, or the perfusion of an analyte/metabolite in fetal or maternal tissues). It should be understood that the apparatus of the present invention may be used for monitoring blood or tissue parameters of a human being.

The apparatus 100 includes such main constructional parts as a measurement unit formed by an optical unit 101 including an illumination assembly 101A and a light detection assembly 101B; and an acoustic unit including a transducer arrangement 110. In the present example of FIG. 1A, the detection assembly includes a single detection unit. In this connection, it should be noted that the term "single detection unit" not necessarily signifies a single detector, but may refer to an array of detectors, provided they are associated with the same location with respect to the illuminated region.

The optical and acoustic units are connectable to a control unit 120. The control unit 120 is typically a computer system including inter alia a power supply, a control panel with input/output functions, a memory utility, a data presentation utility (e.g., display), a data acquisition assembly, and a data processing and analyzing utility (e.g. CPU). The control unit 120 includes a signal generator (e.g. function generator) 120A to control the operation of the transducer arrangement 110, and an appropriate utility 120B for operating the optical unit 101. The CPU is preprogrammed for receiving measured data coming from the detection assembly 101B and processing this data to determine the desired parameter, e.g., oxygen saturation of the fetus.

In the present example, the optical unit 101 is configured as a portable probe including a support structure 103 carrying at least a part of the illumination assembly 101A and at least a part of the detection assembly 101B. The illumination assembly 101A is preferably configured for generating light of at least two different wavelengths. To this end, the illumination assembly may include at least two light emitters (e.g., laser diodes), one emitting narrow bandwidth photons of a wavelength within the range of 605 nm to 805 nm and the other emitting photons of a wavelength within the range of 800 nm to 1300 nm. The illumination assembly 101A may for example be preprogrammed to produce the different wavelength components at different times, or simultaneously produce wavelength components with different frequency- and/or phase-modulation. Accordingly, the control unit 120 is preprogrammed to identify, in a signal generated by the detection assembly 101B, the corresponding wavelength of the irradiating light, using time, phase or frequency analysis.

The illumination assembly 101A may include light emitter(s) carried by the support structure 103 and communicating with the control unit 120 via an output port 121 of the light emitter(s) using wires 106 or wireless signal transmission. Alternatively, the light emitter(s) may be located outside the support structure 103 (e.g., within the control unit 120) and a light guiding assembly 106 (e.g., optical fibers) is used for guiding light to the output port 121 located on the support structure 103.

The detection assembly 101B includes one or more light detectors. This may be a photomultiplier tube, or preferably an image pixel array, e.g., CCD or an array of photodiodes. It should be noted that, for the purposes of the present invention, an input port 122 of the detection assembly 101B is larger than that used for imaging by means of diffuse light. In diffuse light imaging, localization is achieved by small input ports, otherwise light from a large volume is collected. According to the invention, light collection from a large volume is desired, since localization is achieved by the ultrasound tagging. Hence, the input port 122 of the detection assembly 101B is optimized to collect light from a substantially large volume of tissue and/or blood, for example by using large area detectors or CCD cameras or an array of detectors comprising a single input port.

As indicated above, the detection assembly 101B may include two separate detectors or an array of detectors. Each detector may be coupled to a bandpass filter configured for transmitting light of a corresponding one of the wavelengths produced by the illumination assembly 101A. The bandpass filters may include high-pass, low-pass and bandpass optical filters. Alternatively narrow bandwidth detectors can be used.

It should be understood that the detector(s) may be accommodated outside the support structure (probe) 103, e.g., may be located within the control unit 120, and returned light (light response) may be guided from the input port 122 of the detection assembly via light guiding means 105 (e.g., optical fibers). It should also be understood that the connectors 105 and 106 may be electric wires connecting the control unit 120 to the illumination assembly and detection assembly located on the probe 103, or the connection may be wireless.

Thus, generally, the terms "illumination assembly" and "detection assembly" or "detection unit" as carried by a support structure which is brought in contact with a human body, are constituted by at least light transmitting and receiving ports. Probes (kits) of the present invention including light transmitting and receiving ports and preferably also acoustic ports, will be described further below with reference to FIGS. 6A-6B and 7A-7B.

The control unit 120 (its signal generator 120A and CPU) is connected to the transducer arrangement 110 using cables 107 and/or using wireless means.

Figure 1B:
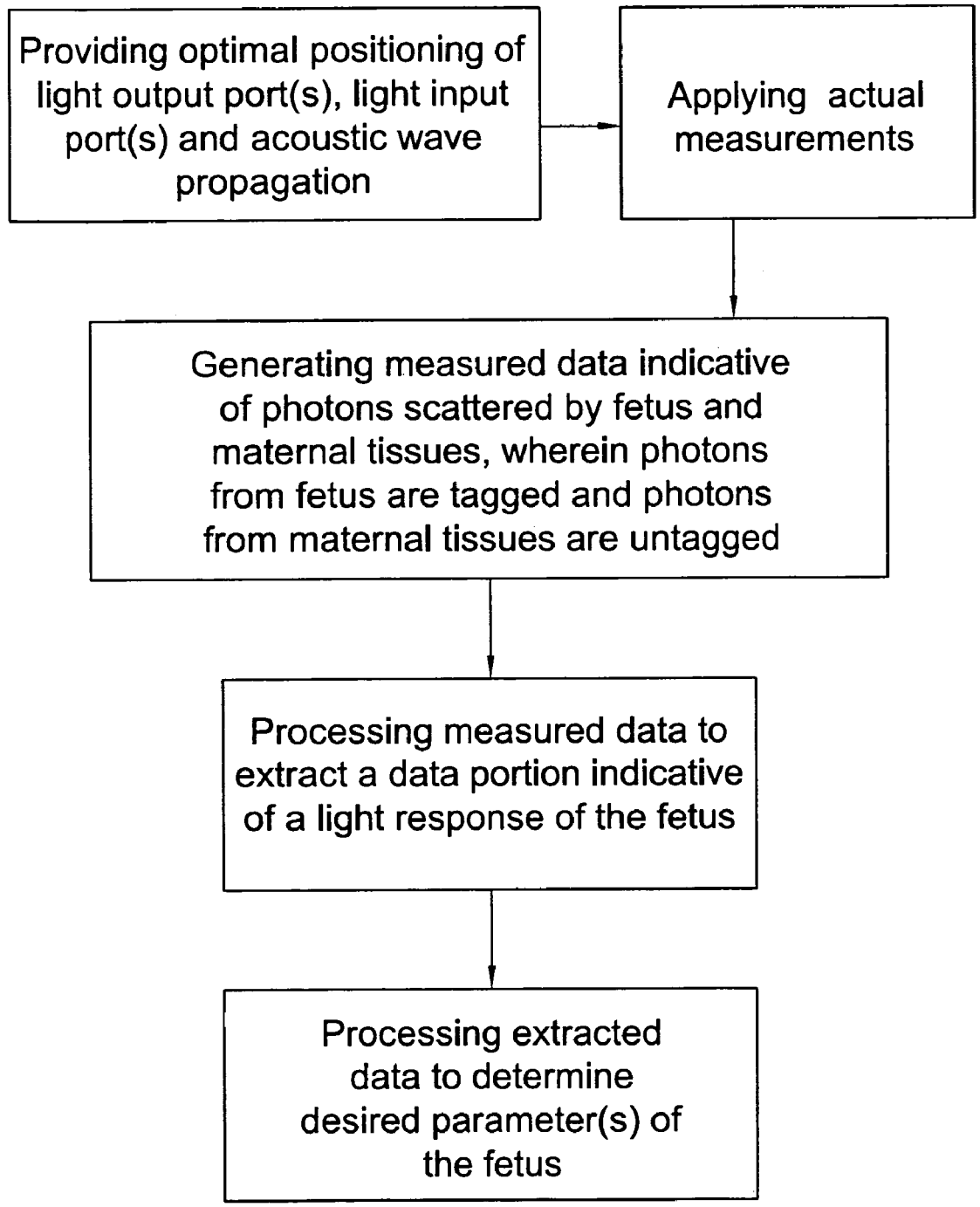
FIG. 1B exemplifies an operating method of the apparatus of FIG. 1A.

An example of a monitoring method of the present invention, using the apparatus 100, will now be described with reference to FIG. 1B.

Step 1: Prior to performing the actual measurements, an optimal positioning of the assemblies of the optical unit and of the acoustic unit with respect to a region of interest (fetus) is provided to satisfy an operating condition for measurements. The operating condition is such that both light (at least a portion of the illuminating light) and the acoustic radiation irradiate the same region (volume) simultaneously, while substantially not overlapping in outside regions (maternal tissues 11); and that the detection assembly detects light scattered from both the region of interest and regions outside thereof. Preferably, the region where the ultrasound and light overlap is the region of interest (fetus 2), but generally a region outside the region of interest may be selected to be overlapping region. Generally speaking, the positioning of the optical unit and transducer arrangement with respect to the fetus 2 is such as to enable distinguishing between scattered photons collected from the maternal tissues 11 and from the fetus 2 using ultrasound tagging of light.

This pre-positioning utilizes an ultrasound imaging of the region of interest. To this end, an imaging system of any known suitable configuration may be used, which may utilize the same transducer arrangement 110 used for the measurement process or another ultrasound transducer(s). Ultrasound images of the maternal tissues 11 (e.g. abdomen, uterus) and of the fetus 2 are acquired and analyzed by the control unit 120 (which in this case is installed with a suitable image processing utility) or another appropriately preprogrammed computer system, to determine the optimal positioning of the optical unit 101 (namely the illumination assembly 101A and the detection assembly 101B) relative to the fetus and relative to the acoustic unit 110.

It is important to note that according to the invention, ultrasound tagging is utilized for the purposes of "tagging" a light response from a selected region of interest (fetus), thus enabling processing of detected tagged and untagged light portions to identify the light response of the selected region of interest. This is contrary to the known techniques where ultrasound tagging is used for imaging purposes to enable two and three-dimensional imaging.

The illumination assembly 101A is preferably placed at the shortest distance to the fetus 2, preferably to the fetal head. It should be understood that other organs or tissues of fetus 2 may be chosen for measurements as well. Preferably, the illumination assembly 101A is placed such that a light path between the illumination assembly 101A and the fetus 2 is that suffering the least attenuation at the wavelengths chosen for measurements, as compared to the other paths. The distance between the illumination assembly 101A and the detection unit 101B is preferably determined to be at least equal to and preferably larger than the distance between the illumination assembly 101A and the head of the fetus 2.

Preferably, the support structure 103 is configured to define various positions for attaching the detection unit 101B and/or the illumination assembly 101A to be at the correct distance between them. For example, these positions may be determined by using a sliding bar (not shown) that is attached to the light detection unit 101B and can be secured to the support structure 103 using a small screw or a latch. Alternatively, a plurality of light output ports and/or plurality of light input ports are provided on the support structure 103 and the control unit 120 operates to select the appropriate light source(s) and detector(s) (light output port and light input port) for measurements. This selection is based on the signals generated by each detector and on the geometry of the maternal tissues and the position of the fetus.

Additionally, the illumination assembly 101A and the detection unit 101B are placed such that the light output port 121 of the illumination assembly and the light input port 122 of the detection assembly are in close contact with an outer skin 10 of the maternal abdomen. Optionally, an index matching oil or adhesive is used to reduce reflection of light from the outer skin 10. The adhesive may be used to secure the apparatus 100 to a specific location on the maternal abdomen. Alternatively, or additionally, a belt can be used to prevent movement of the apparatus 100.

Once the position of the illumination assembly 101A and the detection assembly 101B is fixed, the ultrasound transducer arrangement 110 is positioned such that acoustic waves 150 generated by the transducer arrangement 110 are coupled into the maternal abdomen, propagate through uterus and amniotic fluid, and reach the fetus 2. For example, in the case the illumination assembly 101A and detection assembly 101B are appropriately placed to illuminate and collect light scattered by the fetus head, the transducer 110 is placed such that the acoustic waves 150 propagate through the same region of the head from which scattered photons 155 are detected by the detection assembly 101B. The transducer 110 may be fixed to an appropriate location using an ultrasound transmitting adhesive or using gel for acoustic coupling, and optionally a belt for fixing the transducer to one location. Alternatively, the ultrasound transducer arrangement 110 is configured as a phased array transducer producing a focused beam that is being scanned over a region of skin 10 overlaying the maternal tissues 11.

Step 2: Having optimally positioned the illumination assembly 101A, detection unit 101B and ultrasound transducer arrangement 110, measurements are taken by appropriately operating the apparatus 100. The control unit 120 actuates the illumination assembly 101A to generate photons 155 of at least two wavelengths. The photons 155 propagate through maternal tissues, through the uterine wall, and reach the fetus 2. A portion of photons 155 is absorbed by hemoglobin in the fetus blood, and a portion of photons 155 is scattered by tissues and cells of the fetus 2 and of the mother. A portion of the scattered photons 155 propagates through the maternal tissues 11 and reaches the detection assembly 101B. The latter collects at least a part of this portion of the scattered photons 155 and generates measured data indicative thereof, i.e., an electric signal in response to the number of photons that are collected at the input port 122 of the detection unit at a specific point in time for each irradiating wavelength generated by the illumination assembly 101A.

It should be noted that, in the case the detection assembly 101B is spaced from the illumination assembly 101A a distance equal to or larger than twice the minimal distance between the fetus 2 and the illumination assembly 101A, the detection unit 101B collects both back and forward scattered photons. In the case the illumination assembly 101A includes a laser with a coherence length larger than the optical path of scattered photons in the tissue, an interference pattern resulting in a speckle image is generated on the input port 122 of the detection assembly. In order to detect and analyze the speckle image, the detection assembly 101B may include an array of detectors with an individual size comparable to that of individual speckle. The illumination assembly 101A may be configured and operable to produce a continuous stream of photons 155 (CW), or a time modulated stream (at a certain frequency W), or a train of pulses.

In the present example of FIG. 1A, a portion of detected photons scattered by the fetus 2 are tagged by ultrasound waves, while detected photons scattered by the maternal tissues 11 are untagged. As photons 155 illuminate the fetus 2, the transducer 110 generates acoustic waves 150 that propagate through maternal tissues to irradiate the same volume of the fetus 2 from which scattered photons 155 are detected by the detection assembly 101B. The interaction of acoustic waves 150 with photons 155 results in that the frequency of photons 155 is shifted by the frequency of acoustic waves 150 (acousto-optic effect). These frequency-shifted or frequency-modulated photons are thus "tagged" and can be identified. The detection assembly 101B detects both the frequency shifted photons ("tagged photons") and the photons at the original frequency ("untagged photons") at both wavelengths. The detection assembly 101B generates measured data (electric signals) in response to both the tagged and untagged photons.

Step 3: The control unit 120 processes the measured data using an appropriate algorithm according to the type of detection used. For example: in the case of a single (large area) detector, heterodyne detection (e.g., as described by [Lev A. and B. G. Sfez Optics Letters (2002) 27 (7) 473-475]) is used to separate data indicative of the signal of the tagged photons; when a CCD camera is used and a full speckle image is detected, the technique described by [Leveque-Fort et al. in Optics Communication 196 127-131 (2001)] is used to determine the optical signal of photons scattered from the particular volume which is tagged by ultrasound waves.

Using the above, or other suitable, techniques, it is possible to determine the effective attenuation of photons 155 as they propagate through the fetus 2. To this end, ultrasound radiation may be applied such that acoustic waves 150 propagate through different depths of the fetal tissues (e.g., by displacing the transducer arrangement with respect to the body or by using a phase array transducer). Accordingly, the absorption coefficient and the reduced scattering coefficient can be isolated in the two wavelengths chosen for illumination. For example, using a similar equation to equation 4 of Lev et al. referenced above:

$$x = \frac{\gamma_6^O - \frac{\mu_{eff,6}}{\mu_{eff,8}}\gamma_8^O}{\left[(\gamma_8^H - \gamma_8^O) - \frac{\mu_{eff,6}}{\mu_{eff,8}}(\gamma_6^H - \gamma_6^O)\right]}$$

it is possible to determine the oxygen saturation level of the fetus. Here, x is the fraction of deoxyhemoglobin, $\gamma$ are the molar extinction coefficients of oxyhemoglobin(O) and deoxyhemoglobin (H) at both wavelengths (in the referenced paper, 6 stands for 690 nm and 8 for 820 nm) and $\mu_{eff,6}$ and $\mu_{eff,8}$ are the measured attenuation coefficients at 690 and 820 nm, respectively.

The ultrasound transducer 110 is kept at a specific location, which is optimal for propagating acoustic waves through the same volume of the fetal body (such as the head) from which scattered photons 155 are detected by the detection assembly 101B. The beam size of transducer 110 is such that the cross section volume between photons 155 and acoustic waves 150 is as large as possible, whether focused or not, for increasing the signal to noise ratio (SNR) of the detection system, without compromising the sensitivity to detect only the fetal oxygen saturation and not the maternal one.

As indicated above, the present invention utilizes ultrasound tagging for the purposes of distinguishing between light responses of the regions of the fetus 2 and the region of maternal tissues 11. Preferably, the frequency of acoustic waves generated by the transducer arrangement 110 is in the range of 50 kHz-8 MHz, and more preferably—lower than 1 MHz. This frequency range provides a better SNR for ultrasound tagged light, as it increases the fraction of photons that are tagged, but results in a lower focusing resolution. This is in contrast to imaging modalities known in the art, where it is desired to improve the imaging resolution and thus higher frequencies and minimal cross section are conventionally chosen. In addition, the detection assembly 101B collects forward and back scattered photons according to the preferred geometry of FOSM 100. Therefore, a number of photons collected by the detection assembly 101B is higher than in cases of reflection based imaging disclosed in the above references, thus enabling an improved SNR. Hence, the invention enables using safer light energies for illumination. It should be understood that such a configuration, although rendering high resolution imaging more complicated than the case where primarily back scattered photons are detected, is highly suitable for fetal oximetry.

The control unit 120 analyzes both back and forward scattered tagged photons to determine the optical attenuation of light propagating through the fetal head. Consequently, the control unit 120 needs not perform high resolution imaging of the fetus, but rather just analyze the collected photons 155 scattered by a large volume of the fetal tissues.

Step 4: The control unit 120 processes that portion of the measured data, which is associated with tagged photons scattered from the fetus (identified as described above), to determine the desired parameter of the fetus—oxygen saturation in the present example. Two modalities can optionally be used to determine the oxygen saturation level of a fetus intrautero, one being based on measuring the average oxygen saturation level (known as oximetry) and the other being based on measuring the oxygen saturation level correlated with changes in the blood volume during the cardiac cycle (known as pulse oximetry).

Oxygen saturation S is a ratio between the concentration of oxygenated hemoglobin [HbO] and the total concentration of hemoglobin [HbT] in blood:

$$S=[HbO]/[HbT] \; (*100\%) \quad [1]$$

$$[HbT]=[HbO]+[Hb] \quad [2]$$

wherein [Hb] is the concentration of deoxygenated hemoglobin.

The saturation S can be extracted from the attenuation coefficient measured for at least two wavelengths $\lambda_1$ and $\lambda_2$, where the molar absorption and scattering coefficients for Hb and HbO at each wavelength are known in the literature. It should be noted that more than two wavelengths can be used, to improve sensitivity of the measurement.

As the arteries expand, a blood volume [HbT] is increased by [ΔHbT], therefore absorption changes periodically. The optical attenuation at $\lambda_1$ and $\lambda_2$ is measured at predetermined points (for example, the maxima and minima of a power spectrum of the tagged signal or the processed tagged signal, as defined below) generated by the detection assembly 101B during a cardiac cycle. As indicated above, in the present example tagged signal is that associated with the fetus. The saturation S can be calculated from differences in attenuation of light (ΔOD) at each wavelength between maxima and minima.

$$\Delta OD^\lambda = (\mu_{HbO}^\lambda [HbO] + \mu_{Hb}^\lambda [Hb])d = (\mu_{HbO}^\lambda S + \mu_{Hb}^\lambda (1-S))[HbT]d \quad [3]$$

wherein $\mu_{HbO}^\lambda, \mu_{Hb}^\lambda$ are the molar attenuation coefficient of oxygenated and deoxygenated hemoglobin respectively, at wavelength $\lambda (\lambda = \lambda_1, \lambda_2)$ and d is the distance from the source to the target tissue (fetal or maternal).

Defining the ratio R between $\Delta OD^\lambda$ at each wavelength $\lambda_1$ and $\lambda_2$:

$$R = \frac{\Delta OD^{\lambda 1}}{\Delta OD^{\lambda 2}} = \frac{[\mu_{HbO}^{\lambda 1} S + \mu_{Hb}^{\lambda 1}(1-S)]}{[\mu_{HbO}^{\lambda 2} S + \mu_{Hb}^{\lambda 2}(1-S)]} \quad [4]$$

saturation S is extracted from equation [4] when $\Delta OD^{\lambda 1}$ and $\Delta OD^{\lambda 2}$ are measured and the molar attenuation coefficients are known.

According to an embodiment of the present invention, the control unit 120 analyzes signals generated by the detection assembly 101B in response to each wavelength $\lambda_1, \lambda_2$ generated by the illumination assembly 101A. The signals corresponding to tagged photons 155 are selected by the detection assembly 101B using heterodyne detection, or by the control unit 120 using frequency analysis and/or speckle imaging. These signals are termed "tagged signals". The time dependent amplitude and/or phase of the tagged signals for each wavelength $\lambda_1, \lambda_2$ is stored in the memory of the control unit 120, over a specified period of time of at least one fetal heart cycle. To determine the oxygen saturation level of the fetus, the control unit 120 determines the changes in attenuation of tagged signals at each wavelength.

Considering the determination of oxygen saturation of fetus 2 based on oximetry, the time averaged signals generated by the detection assembly 101B in response to the tagged photons 155 of at least two illuminating wavelengths reaching the input port 122, are used to determine the oxygen saturation level. Time averaging can be performed over longer time scales than the duration of a fetal heart cycle.

Considering pulse oxymetry used for determining oxygen saturation of a fetus, the temporal changes (due to the fetal cardiac cycle) in the blood volume of the fetus are monitored by the control unit 120 by monitoring the low-frequency changes (1-2.5 Hz) in the signals generated by the detection assembly 101B in response to the tagged photons 155 of at least two illuminating wavelengths reaching the input port 122 of the detection assembly. Since the ultrasound frequency is orders of magnitude higher than the fetal heart rate, it is possible to average the signals responsive to tagged photons over a fraction of the fetal heart cycle to improve the SNR of the measurement. Using methods of pulse oximetry, both the oxygen saturation and the pulse rate are determined simultaneously.

The control unit 120 displays the determined fetal oxygen saturation level, along with fetal heart rate, as a function of time. Fetal heart rate is determined by low-frequency analysis of the tagged signals. The control unit 120 optionally alerts using a suitable indication utility (e.g. sound and/or light signal), when oxygen saturation level drops below a certain threshold (for example 30% or 40%), or when fetal heart rate changes abnormally.

Preferably, monitoring apparatus 100 provides for calibrating for movements of fetus 2 during the measurement. To this end, the control unit 120 operates to determine the position of fetal head relative to the apparatus 100. This is carried out either periodically, or upon detection of signals not corresponding to a normal heart rate or oxygen saturation level. The control unit 120 sends a control signal to the transducer arrangement 110 initiating an ultrasound echo measurement. In an echo measurement, the transducer arrangement 110 transmits acoustic waves 150 into maternal tissues, and collects acoustic waves 150 reflected by fetal and maternal tissues. The reflected signals are analyzed by the control unit 120 (using any conventional ultrasound imaging technique) to determine a position of the fetal head. If a substantial movement is detected, the control unit 120 sends a signal to the transducer arrangement 110 to optionally change a direction of acoustic waves 150 in a new direction corresponding to a new position of the fetus 2. Additionally or alternatively, the control unit 120 alerts the operator of apparatus 100 to readjust the position of the apparatus accordingly.

Although the above description refers to a single fetus, it should be understood that the technique of the present invention can easily be adapted for monitoring several fetuses intrautero. The location of each fetus is determined using an ultrasound imaging system, and different monitoring apparatuses (i.e., optical and acoustic units) or an integrated multi-fetuses apparatus are used. All the monitoring apparatuses can be hooked to the common control system that controls each apparatus separately, and processes the signals using the same or different processing utilities. A display shows the oxygen saturation level of each fetus separately along with its heart rate and other parameters.

The present invention also provides for advantageously utilizing the principles of ultrasound tagging of light in pulse oximetry for monitoring oxygen saturation in a localized region of interest in a human or animal body (without a fetus). Turning back to FIG. 1A, the optical unit 101 is configured as a pulse oximeter, namely includes an illumination assembly 101A configured to generate light of at least two different wavelengths and a light detector 101B; and is used in combination with the transducer arrangement to significantly improve the pulse oximetric measurements. The monitoring apparatus 100 may be configured to operate in a transmission mode (light transmission based detection), such as the conventional pulse oximeter placed on a finger or earlobe. In this case, the support structure 103 is located such that the illumination assembly 101A is co-linear with the detection assembly 101B: the illumination assembly 101A is placed at one side of the tissue and the detection assembly 101B is placed at the opposite side of the tissue, therefore ballistic and scattered light emitted from illumination assembly 101A are detected by detection assembly 101B. The transducer arrangement 110 is placed such that acoustic waves overlap with an illuminated region in the region of interest from which scattered light reaches the detection assembly 101B, which is preferably the region encompassing a blood vessel (e.g. an artery) or a collection of arterial vessels. In other applications, requiring reflection based detection from a region of interest ("reflection mode"), the apparatus 100 is located as described for the fetus-related application, where the region of interest preferably encompasses a blood vessel (e.g. an artery) or a collection of arterial vessels. Such an arrangement is superior to conventional pulse oximeter as it is not affected by incoherent ambient light, and more importantly is less affected by motion of the tissue relative to illumination and detection assemblies, as long as the region of interest is kept illuminated and the acoustic waves propagate through it.

It should be understood that using the ultrasound tagging of light in the pulse oximetry based measurements significantly improves the measurements, since the measured power spectrum of an ultrasound-tagged light signal is practically insensitive to movements of the region of interest under measurements, which is the common problem of the typical pure pulse oximetry measurements.

Figure 2:
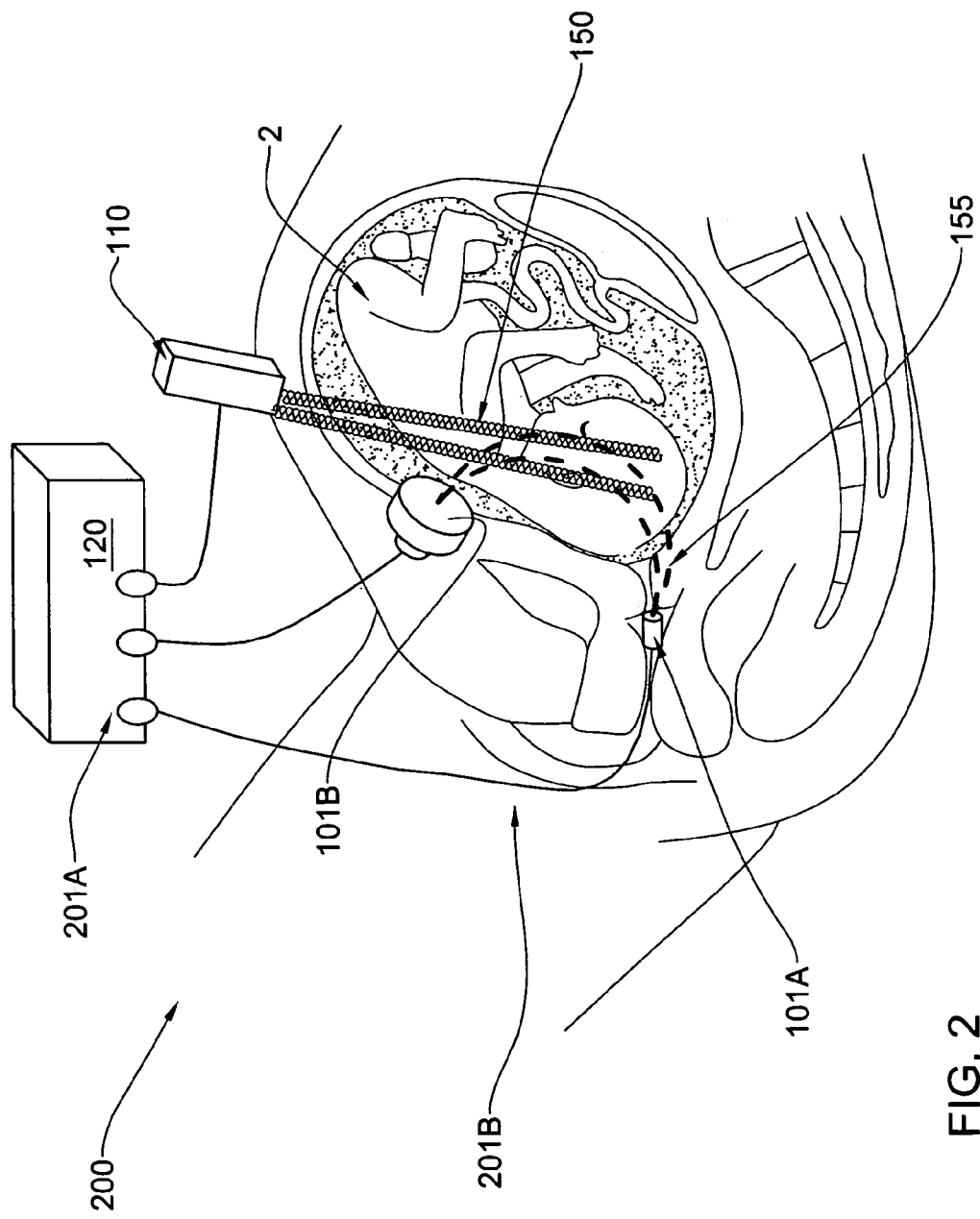
FIG. 2 schematically illustrates a monitoring apparatus, according to another embodiment of the present invention.

FIG. 2 exemplifies another configuration of a fetal oxygen saturation monitor, generally designated 200, of the present invention. To facilitate understanding, the same reference numbers are used for identifying components that are common in all the examples of the invention. In the apparatus 200, an illumination assembly 101A includes a light source 201A mounted within a control unit 120 and an optical fiber 201B guiding light from the light source to the region of interest (fetus). The optical fiber 201B is inserted into the vaginal track of the pregnant woman (using suitable means, for example a flexible support structure which is not specifically shown). The optical fiber 201B is positioned such that it is in close contact with the cervix or to amniotic membranes prior to rupture. Optionally, following membrane rupture optical fiber 201B is attached to the presenting part of the fetal head with the aid of a support structure. A light detection assembly 101B is placed on the maternal abdomen, such that it collects photons scattered by the fetal blood. The detection assembly 101B is connected to a suitable utility of the control unit 120 via wires (as shown in the figure) or wireless. An ultrasound transducer arrangement 110 is also placed transabdominally such that acoustic waves 150 can propagate through the part of the head of a fetal 2 being closest to the optical fiber 201B and detection assembly 101B. In some cases, it may be advantageous to introduce the transducer arrangement 110 also through the vaginal track.

Figure 3A:
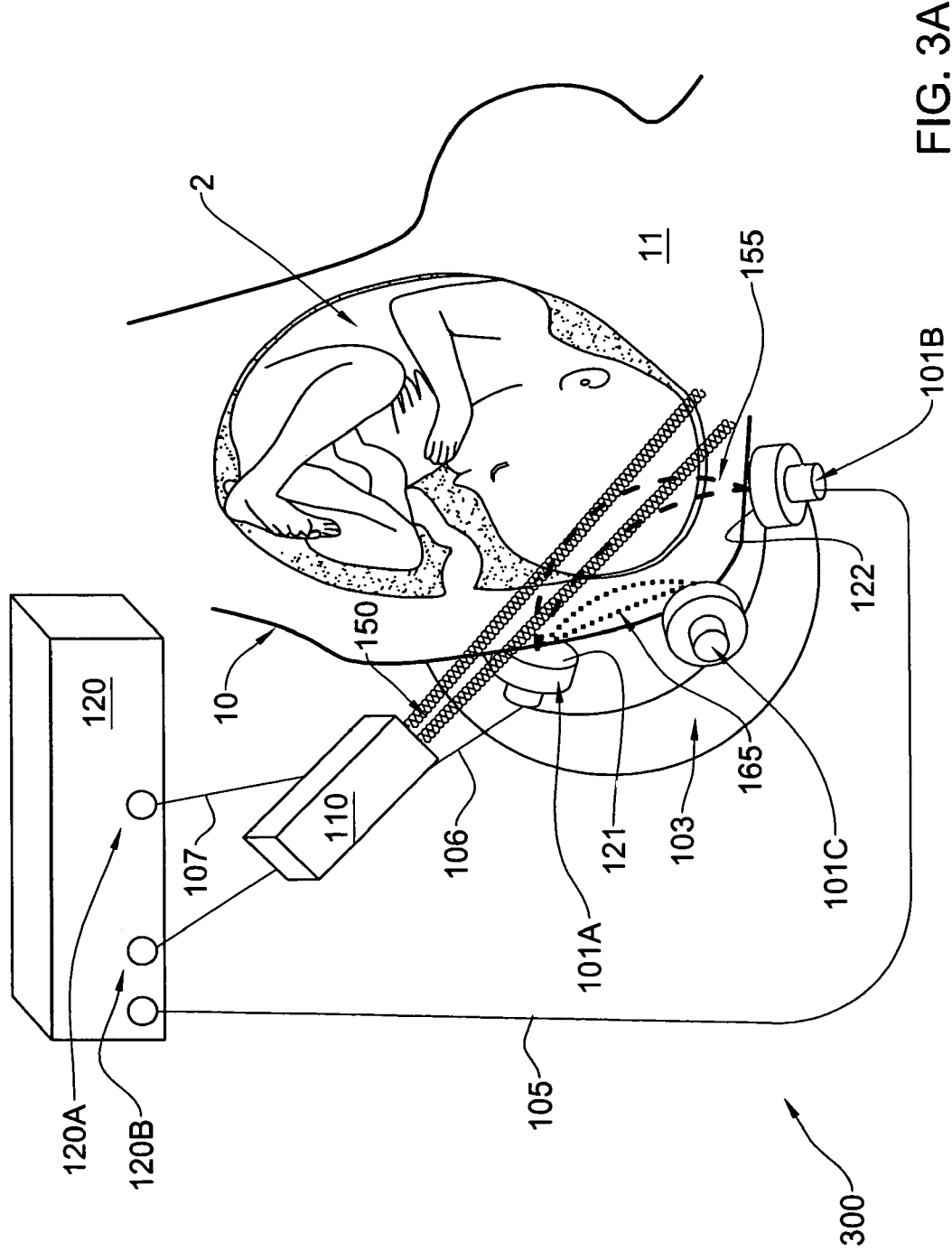
FIG. 3A schematically illustrates a monitoring apparatus according to the invention configured to be capable of monitoring the fetal and maternal oxygen saturation.

Reference is made to FIG. 3A exemplifying a preferred embodiment of a monitoring apparatus 300 according to the invention. The apparatus 300 is configured generally similar to the above-described apparatus 100, namely includes an acoustic transducer arrangement 110, and an optical unit 101 having a probe 103 carrying at least a part of an illumination assembly 101A and at least a part of a detection assembly. Here, the detection assembly is formed by two detection units 101B and 101C associated with different locations with respect to the illuminated region defined by a location of the illumination assembly 101A. The additional detection unit 101C is also attached to the support structure (probe) 103 and is connected to a control unit 120 via electrical cable (not shown) or wireless means.

One of the detection units—detection 101C in the present example, is located in the proximity of the illumination assembly 101A, and the other detection unit 101B is located at a larger distance from the illumination assembly. In the present example, the detection unit 101C is located between the illumination assembly 101A and the detection unit 101B. Generally, the arrangement of the illumination assembly and detection units is such that one of the detection units (detection unit 101C) is located close to the illumination assembly to therefore detect photons 165 scattered from regions outside the fetus 2 (i.e., light reaches the detector 101C prior to reaching the fetus); and the other detector 101B) is more distant from the illumination assembly and thus detects photons 155 scattered from the fetus and propagating through the maternal tissues region and being thereby affected by the maternal tissues.

The transducer arrangement 110 is aligned and/or scanned, such that it transmits acoustic waves 150 to the volume within the illuminated region of the fetus from which photons 155 are detected by the detection unit 101B, and substantially does not irradiate the maternal tissue region from which photons 165 are collected by the detection unit 101C.

Signals (measured data) generated by the detection unit 101C may be used by the control unit 120 to determine the maternal oxygen saturation level and heart rate simultaneously, which may thus be displayed. Generally, the use of the additional detection unit 101C located close to the illumination assembly 101A assists in separating a light response of the fetus region 2 from that of the maternal tissues' region 11, since the detection unit 101C so-positioned will detect scattering effect of light that traveled through the maternal tissues and did not reach the fetus, and which is thus indicative of the maternal region response only. The other detection unit 101B practically detects photons 155 including the tagged response of the fetus and the tagged response of the maternal tissues.

It should be understood that generally the detection unit detects the tagged light response of the fetus affected by the maternal tissues. Hence, the expression "tagged response of the maternal tissues" means photons tagged (by ultrasound) inside the volume of the fetus being scattered by maternal tissue.

Both the tagged and untagged responses of the maternal tissues' region are identically frequency modulated by the mother's heart rate. Hence, the first measured data from the detection unit 101C, which is mainly indicative of the untagged light response of the maternal tissues, can be used to analyze the second measured data from the detection unit 101B to separate a signal indicative of a light response of the fetus from that of the maternal tissues.

Figure 3B:
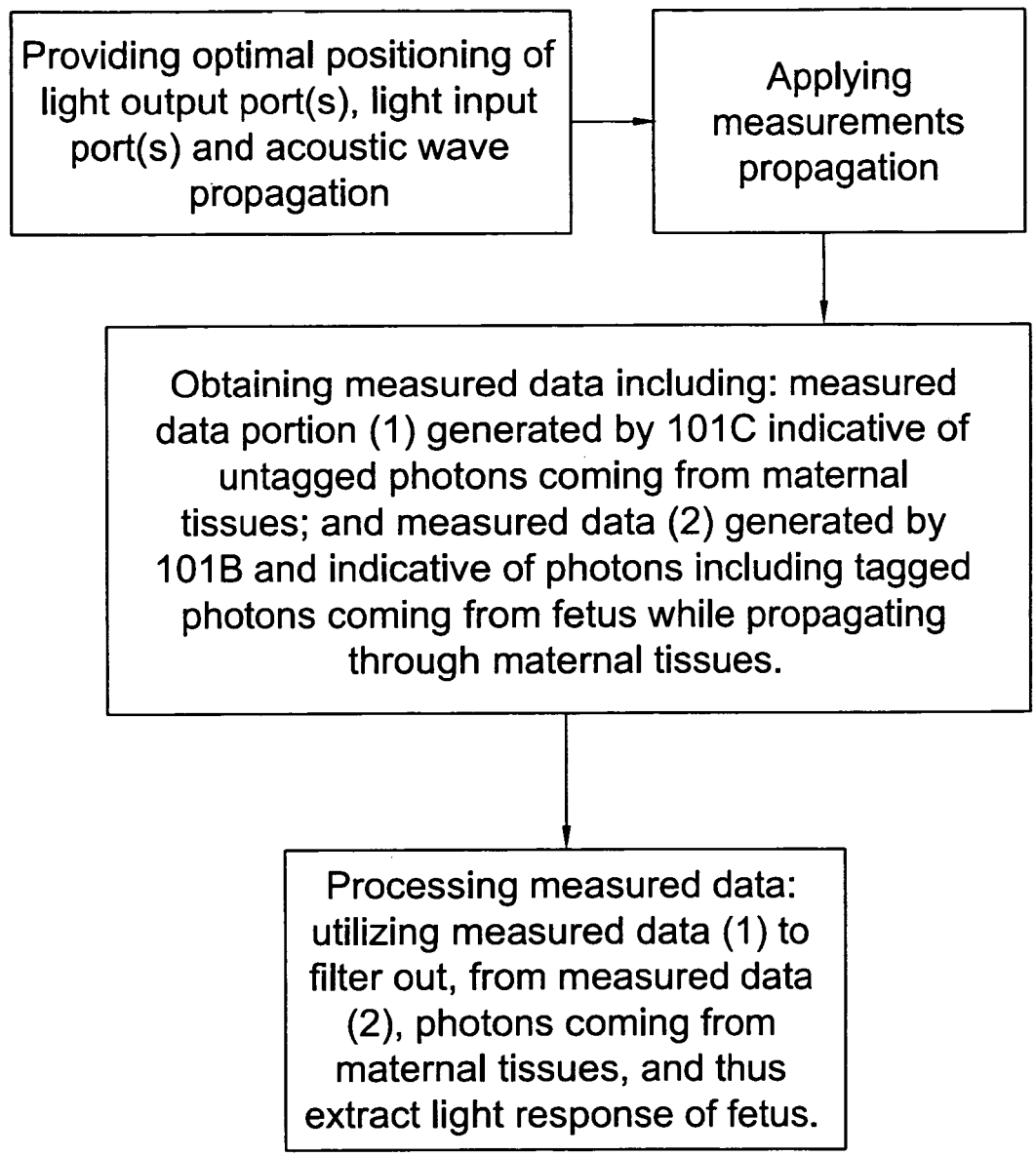
FIG. 3B illustrates a flow diagram of the main steps in a method of the invention using the apparatus of FIG. 3A.

FIG. 3B illustrates a flow chart of the main operational steps of a method of the invention utilizing the monitoring system 300.

Step 1: First, optimal positioning of the illumination assembly, detection assembly and acoustic transducer arrangement is provided as described above. This positioning ensures that acoustic waves interact with the region of interest (fetus volume) from which photons 155 are detected at the detector 101C and substantially do not interact with the region outside the region of interest (maternal tissues) from which photons 165 are detected by the detector 101C.

Step 2: Actual measurements are performed when at the optimal positions of the illumination, detection and acoustic assemblies. Measured data includes: (1) a first data portion generated by the detection unit 101C and indicative of the untagged photons coming from the maternal tissues; and (2) a second data portion generated by the detection unit 101B and indicative of the photons including tagged and untagged photons coming from the fetus, and untagged photons coming from the maternal tissues.

Step 3: The measured data is processed to filter out, the contribution of tagged and untagged photons scattered by regions outside the region of interest, to the measured signal, wherein this contribution is identified as that having frequency modulation by the mother's heart rate, as previously identified from the data portion (1). Hence, the so-separated light response of the fetus can be processed to determine the desired parameter of the fetus. The control unit 120 may use signals generated by the detection units 101B and 101C to determine fetal and optionally maternal oxygen saturation levels.

More specifically, the apparatus 300 operates as follows: The illumination assembly 101A simultaneously generates photons of two different wavelengths (generally, at least two wavelengths). Photons denoted 155 are photons scattered from maternal and fetal tissues and reaching an input port 122 of the detection unit 101B, i.e., photons scattered from a tagged volume of tissue, that is intermittently or continuously radiated by acoustic waves 150 generated by transducer 110.

The transducer arrangement 110 may, for example, be operated to generate a burst of acoustic waves, with a delay of at least $t_{on}$ between the end of one burst and the onset of another burst. Time to is the time it takes the acoustic burst to reach the target fetal tissues (e.g. head). The duration of the burst $\Delta t_0$ is determined such that at time $t_f$, bounded by a condition $t_0 \leq t_f \leq (t_0 + \Delta t_0)$, the acoustic pulse propagates primarily through target fetal tissues (i.e., through a volume $\Delta V$ of fetal tissues). Therefore, during this time $t_f$ the acoustic burst reaches the target fetal tissues, and acoustic waves are hardly propagating through maternal tissues. A portion of photons 155 propagating through the same volume of fetal tissues during time $t_f$ is tagged. Whereas, photons 165 are those propagating only through maternal tissues at the same time $t_f$ and are therefore untagged (since they did not interact with the ultrasound irradiated region).

The detection unit 101C is placed at a distance Q from the illumination assembly 101A, such that its input port collects primarily photons 165 that are not scattered from the tagged volume. The detection unit 101C is optionally moved until it does not collect tagged photons, and is then fixed in the appropriate position. It should be noted that, alternatively, the detection units 101B and 101C are fixed in place, and a position of the ultrasound transducer arrangement 110 is adjusted to be such that the tagged photons 155, scattered from fetal tissues, primarily reach the detection unit 101B and not the detection unit 101C.

Figure 3C:
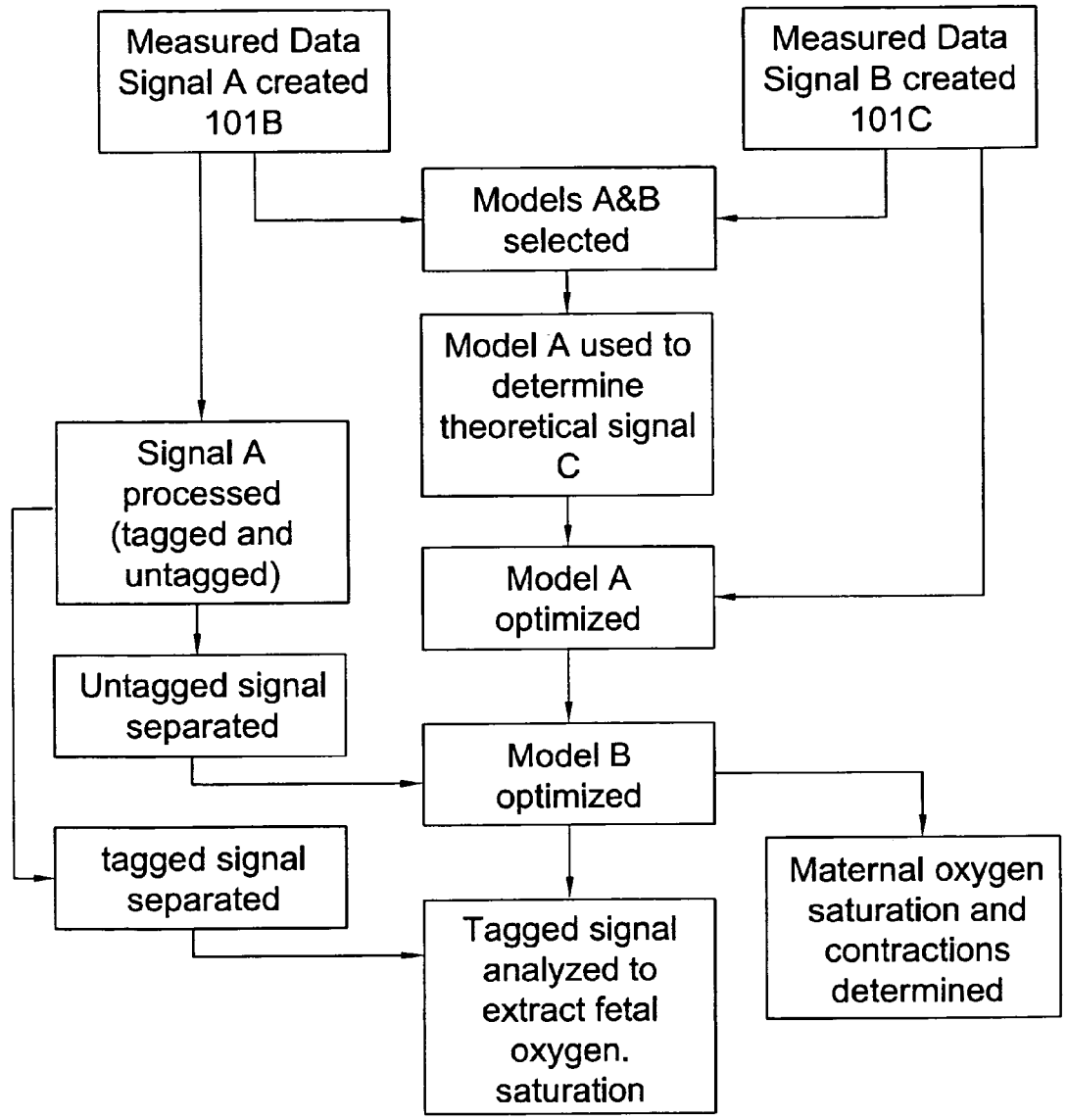
FIG. 3C shows a flow diagram of a specific example of the method of FIG. 3B.

FIG. 3C more specifically exemplifies the data processing procedure for processing measured data from the apparatus 300. The detection unit 101B receives photons 155 including tagged and untagged photons scattered by the uterus and tagged photons scattered by the fetus, while the detection unit 101C receives primarily only untagged photons 165 scattered by the maternal tissues. A signal that is generated by the detection assembly 101B in response to collected photons 155 is referred to as "signal A". A signal generated by the detection unit 101C in response to photons 165 is referred to as "signal B".

According to this example, two models are used to describe the propagation of light in a multi layer tissue system. Such models are described for example by Keinle et al. in Physics in Medicine and Biology 44: 2689-2702 (1999). One model (Model A) includes the parameters representing some of the tissues through which photons 165 propagate from the illumination assembly 101A through a medium until they reach the detection unit 101C, and the other model (Model B) includes the parameters representing some of the tissues in the medium through which tagged photons 155 propagate until they reach the detection unit 101B. The models include known parameters, such as the molar absorption and scattering coefficients of blood cells, and of oxygenated hemoglobin and deoxygenated hemoglobin at each of the wavelengths of illuminating photons. In addition, the models may include the thickness of the layers (maternal and fetal), presence and volume of amniotic fluid in the light path and other parameters that are measured during the operation of apparatus 300 (as described above with reference to apparatus 100 of FIG. 1). Some tissue parameters in the model may be averaged or other manipulations of the known or measured parameters of the real tissues in models A and B may be carried out.

Given a certain source amplitude, and the known separation between the illumination assembly 101A and the detection unit 101C, model A is used to calculate the expected time dependent photon flux, or light intensity at the input port of the detection unit 101C. The expected time dependent photon flux or light intensity is used to calculate the expected signal (termed "signal C") that can be generated by the detection unit 101C in response to such a photon flux. Signal C actually presents theoretical data for untagged photons at the location of detection unit 101C, while signal B presents real measured data for untagged photons collected by the detection unit 101C. The parameters of model A are adjusted such that signal C is made equal to or closely resembles signal B (best fitting). Signal processing techniques based on optimization algorithms, such as neural network, can be used to optimally determine the parameters of model A. The parameters are used to calculate the optical properties of some of the tissues through which photons 165 propagate.

Additionally or alternatively, certain parameters of models A and B (such as thicknesses of maternal tissues, in particular uterine wall, and/or tensions of muscles) may be unknown, and be determined during operation. During contractions, the thickness of the uterine wall and the tension of the muscles change. Controller 120 determines the thickness of the uterine wall as a function of time by optimizing primarily this parameter of model A. Once determined, these parameters are used to determine contractions' duration and amplitude. Alternatively, tissue velocity measurements are performed by ultrasound assembly 110, using techniques known in the art for echocardiography. Transducer arrangement 110 emits acoustic pulses (not shown) that are reflected back by uterine muscles. The reflected pulses are Doppler shifted with respect to the emitted acoustic pulses. Controller 120 analyzes the reflected signals to determine the thickness and velocity of the muscles. During contractions the thickness and velocity change, therefore controller 120 monitors these changes as a function of time. Consequently, controller 120 displays the amplitude and duration of the contractions. The apparatus 300 thus provides information needed to monitor the progression of labor (contractions' duration and amplitude) in addition to fetal well being (heart rate and oxygen saturation).

In addition, signal B is optionally used to extract maternal oxygen saturation level, by using the time dependent amplitudes of the signals generated by the detection unit 101C in response to photons 165 of at least two wavelengths.

It may generally be assumed that the optical properties of tissues outside the region of interest (outside fetus) through which both photons 155 and 165 propagate are similar (for example maternal abdominal tissues). Alternatively, it may be assumed that by determining the parameters and optical properties of the tissues through which photons 165 propagate, one can deduce, within a reasonable error, the optical properties of corresponding tissues (e.g., other areas of maternal abdominal tissues) through which photons 155 propagate. The parameters calibrated by signal B and the optical properties of the tissues through which photons 165 propagate are then used to calibrate model B that describes the propagation of photons 155 through maternal and fetal tissues.

The time dependent amplitude of signal A at all wavelengths of photons 155 is processed by the control unit 120 using techniques known in the art, such as digital Fourier transformations and analog or digital filtering, to extract, from the entire signal A, a signal portion corresponding to the tagged photons 155. This signal portion is termed "tagged signal A". Tagged signal A is that modulated at the ultrasound frequency generated by the transducer arrangement 110. The amplitude of the power spectra of the tagged signal A at the ultrasound frequency (or related to the ultrasound frequency), the modulation width of its power spectra or other features of tagged signal A, such as its phase, are termed together as "processed tagged signal A" This processed tagged signal A is actually indicative of both the maternal tissues response and the fetus response tagged by ultrasound. In addition, the signal A contains information which is not modulated at the ultrasound frequency, termed "untagged signal A".

According to this specific embodiment, untagged signal A may also be used in the data processing and analyzing procedure, for example to determine some of unknown parameters of model B and further optimize this model. For example, untagged signal A may contain signals which are modulated by maternal cardiac cycle, and have a modulation frequency of 0.5-2 Hz corresponding to maternal heart rate $F_m$. Signal B is also modulated at the same frequency, as photons 165 propagate through maternal tissues containing the same pulsating blood. Consequently, untagged signal A and signal B may be used to calibrate model B relative to model A, where differences and similarities between untagged signal A and signal B are used to optimize the parameters of model B.

In addition, tagged signal A and/or processed tagged signal A are also modulated at maternal heart rate, as tagged photons 155 pass through maternal tissues before and after they pass through the tagged volume. Consequently, tagged signal A and/or processed tagged signal A modulated at this low frequency may be used in conjunction with untagged signal A and/or signal B to extract the portion of tagged signal A that is affected by absorption by fetal blood. This portion calculated for all wavelengths of photons 155, is used to extract the fetal oxygen saturation level.

According to another embodiment of the invention, only tagged signal A and untagged signal A at all the wavelengths of photons 155 are used to extract fetal oxygen saturation levels. According to yet another embodiment, tagged signal A and/or processed tagged signal A are used to determine fetal oxygen saturation at all fetal heart rates $F_f$, where $F_f > F_m$ (or more precisely $F_f > F_m + BW$, where BW is the bandwidth of the detection system, as fetal heart rate is usually faster than maternal heart rate). First, tagged signal A is extracted (separated) by the control unit 120 as described above. Then, the modulation amplitudes of tagged signal A and processed tagged signal A at $F_f$ and $F_m$ are determined. Tagged photons 155 are modulated at $F_f$, however a modulation at $F_m$ may also exist, as tagged photons 155 also propagate through maternal tissues. When this modulation is small, its contribution at higher harmonics (i.e., $2F_m$, $3F_m$) is negligible. The amplitudes of tagged signal A, processed tagged signal A and untagged signal A modulated at frequency $F_m$ are optionally used to determine certain tissue parameters in model B. Using these parameters, tagged signal A is calibrated to correspond primarily to fetal contributions. Fetal oxygen saturation is extracted from features (such as the modulation amplitude, the bandwidth of the modulation, autocorrelation etc.) of the calibrated tagged signal A and/or processed tagged signal A modulated at $F_f$ at all wavelengths of photons 155.

In some cases where the modulation of tagged signal A at $F_f$ in the range of $2F_m - BW < F_f < 2F_m + BW$ can not be neglected, signal B and untagged signal A are used to determine fractions of tagged photons 155 that are modulated by maternal blood, by fitting the parameters of models A and B as described above. Once the parameters are determined, fractions of tagged photons 155 that are modulated by maternal blood and fetal blood can be determined using known methods, for example such as Monte Carlo simulations. Using the results of the simulations, tagged signal A is calibrated to correspond primarily to fetal contributions. The calibrated signal is then used to extract fetal oxygen saturation levels as described above.

Turning back to FIG. 3A, it should be noted that the acoustic transducer arrangement may be accommodated such that acoustic waves propagate towards the fetus along an axis passing between the illumination assembly and the detection assembly. For example, the transducer arrangement or its associated ultrasound port is located on the same support structure 103. The optical unit is preferably operated to start illumination/detection a certain predetermined time after the generation of the acoustic radiation, which is the time needed for the acoustic radiation of a given frequency to arrive at the region of interest (fetus). This ensures that light detected by the detection unit 101C is not affected (tagged) by the acoustic radiation.

Alternatively or additionally, the apparatus of the present invention, for example configured as the above-described apparatus 300, can be used to monitor the optical properties of the amniotic fluid surrounding the fetus. In this case, a region within the amniotic fluid presents a region of interest, and as indicated above the term "maternal tissues" refers to regions outside the region of interest. Optical properties of the amniotic fluid may include, for example, the absorption coefficient, the scattering coefficient, the reduced scattering coefficient and the refractive index of the fluid. Such optical properties are used to calculate the concentration of lamellar bodies, blood or meconium dispersed within the amniotic fluid. The calculated concentration is optionally compared to a threshold level as described below.

Figure 3D:
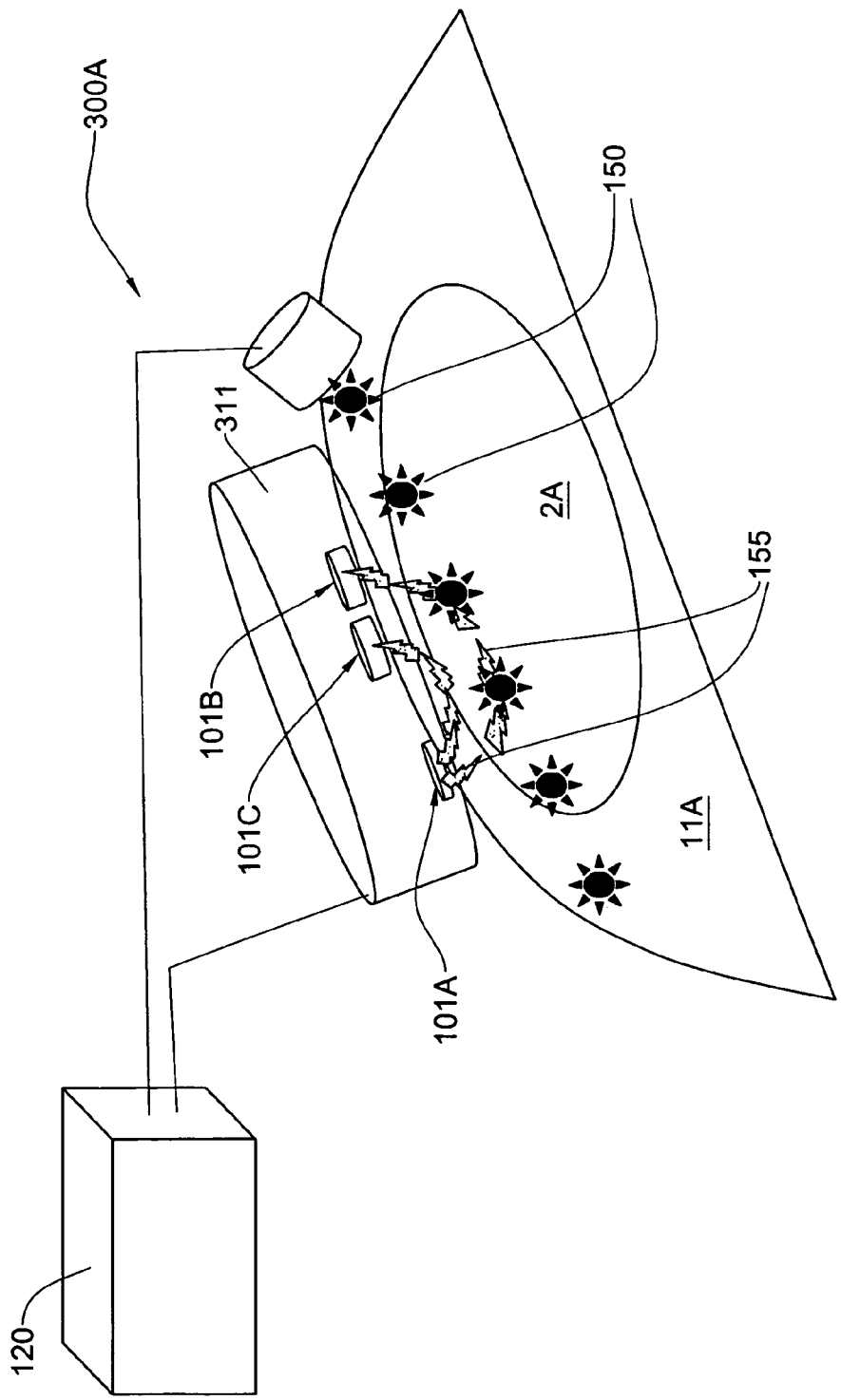
FIG. 3D schematically illustrates yet another example of a monitoring system of the present invention configured for monitoring the amniotic fluid condition.

As illustrated schematically in FIG. 3D, to monitor amniotic fluid, apparatus 300A is configured and positioned similar to the above-described apparatus 300, whereas the region of interest 2A is defined by a substantial volume of amniotic fluid, being at the shortest optical path to light output and/or input ports of illumination and detections assemblies. The substantial volume is that which allows for an overlap of illuminating light and an ultrasound beam within that volume. For example, in the case the illumination assembly 101A and detection unit 101B are appropriately placed to illuminate and collect light scattered by the amniotic fluid 2A, a transducer arrangement 110 is placed such that acoustic waves 150 propagate through the same region of the amniotic fluid 2A from which scattered photons 155 are detected by a detection unit 101B. Preferably, the detection assembly is configured such that a detection unit 101C collects untagged photons propagating through maternal tissues 11A (a region outside the region of interest), and the detection unit 101B collects tagged and untagged photons propagating through a substantial volume of the amniotic fluid (region of interest).

The apparatus 300A may be used for determining the optimal positioning of illumination/detection and ultrasound assemblies, having a plurality of input and output ports, such that the ultrasound beam is scanned over different locations inside the body and the autocorrelation or power spectrum of signals generated by each detection unit are determined by a controller 120 in response to photons scattered from different volumes within the body overlapping with the ultrasound beam. As the line-width of the autocorrelation or power spectrum of the tagged signals, around the frequency of the ultrasound radiation, is different when tagging is performed inside a fluid volume than when performed in a tissue or bone volume, the controller 120 can determine, by monitoring the line width, when the ultrasound beam is used to optimally tag a volume of the amniotic fluid.

For monitoring amniotic fluid, the illumination assembly 101A includes one or more light sources generating a plurality of wavelengths (either simultaneously or sequentially) from 300 nm to 12 μm. For example, a plurality of wavelengths that are absorbed and/or scattered by lamellar bodies contained in amniotic fluid is chosen for determining the concentration of lamellar bodies. Preferably, the plurality of wavelengths is less absorbed by water. Such wavelengths may be chosen in the range of near infrared, i.e., 600 nm-1300 nm.

At each wavelength, the control unit 120 optionally determines models A and B (as described above) for the overlaying maternal tissues 11A (region outside the region of interest) and the amniotic fluid (region of interest), and determines tagged and untagged signal A and untagged signal B as described above. Processed tagged signal A and calibrated tagged signal A are used to determine the reduced scattering coefficient and the absorption coefficient of the tagged volume of amniotic fluid as explained below.

The control unit 120 then determines the concentration of lamellar bodies, blood or meconium in the amniotic fluid. The output of the control unit 120 is displayed on the integrated display or communicated via wireless means or cables to another display or electronic processor. Possible outputs include but are not limited to a light signal indicating higher or lower concentration of lamellar bodies relative to a predetermined threshold, a number shown on the display corresponding to the concentration of lamellar bodies in addition to a display of the threshold number for that value, a sound indicating high or low concentration of lamellar bodies relative to a threshold. The control unit 120 optionally displays a "mature" or "premature" signal, without quantitative information about the concentration of lamellar bodies, or displays "stained" or "clear" signal for the case of meconium staining.

Lamellar bodies are produced by type II alveolar cells in increasing quantities as fetal lungs mature. They are composed almost entirely of phospholipid and represent the storage form of the surfactant. Their diameter is about 0.5-2 μm, and their index of refraction is about 1.475. Consequently, when using the above wavelengths range, it is clear that Mie scattering dominates the scattering process of light from lamellar bodies. Choice of specific wavelengths depends on the optimal signal to noise ratio (SNR) of the apparatus used. The difference in wavelengths used for illumination has to provide a sufficient change in the scattering coefficient that can be detected by the system. The relationship between the wavelength and the reduced scattering coefficient $\mu_{s'}$ of monodisperse scattering dielectric spheres is known in the literature to be:

$$\mu_{s'} = 3.28\pi a^2 \rho \left(\frac{2\pi a}{\lambda}\right)^{0.37} (m-1)^{2.09} \quad [5]$$

wherein α is the radius of the dielectric spheres, ρ is their volume density, λ is the wavelengths in vacuum, $$m = \frac{n_s}{n_0}$$

where $n_s$ and $n_0$ are the refractive indices of the spheres and the surrounding material respectively.

The reduced scattering coefficient $\mu_{s'}$ is related to the scattering coefficient $\mu_s$ using the following equation:

$$\mu_{s'} = (1-g)\mu_s \quad [6]$$

wherein g is the anisotropy factor related to the size and geometry of the scattering centers.

Both the reduced scattering coefficient and the scattering coefficient can be determined according to an embodiment of the present invention.

As an example, light at a plurality of wavelengths is generated by the illuminating assembly 101A. Wavelength selection is based on the absorption and scattering coefficients of the amniotic fluid. For example, amniotic fluid with no blood or meconium absorbs almost equally light at around 735 nm and 780 nm. Therefore, light distributions inside amniotic fluid at these two wavelengths will differ due to wavelength dependant changes of the reduced scattering coefficient of the fluid. This reduced scattering coefficient depends on the size, volume concentration and relative index of refraction of the lamellar bodies (as evident from equation 5 above). Therefore, by determining the reduced scattering coefficients at different wavelengths, the control unit 120 determines the concentration of lamellar bodies in the fluid using equation 5 (or a modified equation 5 which includes physiological parameters of lamellar bodies instead of monodisperse spheres).

In order to determine the presence of meconium in the fluid, a different selection of wavelengths is used. It is known that meconium primarily contains blood and billirubin, therefore at least two wavelengths are used: one that is absorbed by blood or billirubin (for example 660 nm) and the other that is weakly absorbed by either one of them (for example 1064 nm). These wavelengths may for example be used in addition to the above mentioned wavelengths 735 and 780 nm. Irradiating the amniotic fluid with these two wavelengths (e.g., 660 nm and 1064 nm) will result in a different light distribution at the shorter wavelengths when meconium is present than in the case of no meconium. The absorption coefficient of the fluid at these wavelengths is also used to determine the concentration of meconium in the fluid.

The control unit 120 determines the processed tagged signal A at the plurality of wavelengths used to illuminate the tissues, and stores them in memory. Since the time dependant variations in the optical properties of the amniotic fluid are very slow, tagged signal A at each wavelength can be integrated over long periods (much longer than the fetal or maternal heart beats). At those wavelengths, which are absorbed almost equally in the fluid, the variations between the signals obtained at different wavelengths are proportional to the reduced scattering coefficient. From these variations of the measured parameters (listed below), the control unit 120 determines the reduced scattering coefficient.

The control unit 120 determines the reduced scattering coefficient of the amniotic fluid by determining, for each illuminating wavelength, at least one of the following parameters:

(a) The amplitude of the power spectra or autocorrelation of processed tagged signal A corresponding to the frequency of the ultrasound waves;

(b) The line width of the power spectra or autocorrelation of processed tagged signal A (for example, the full width at half max around the frequency of the ultrasound waves);

(c) The spatial attenuation of the amplitude of the power spectrum of tagged signal A corresponding to the ultrasound frequency.

In the latter case, the ultrasound beam scans the illuminated region such that the overlapping volume, within the amniotic fluid, is varied along the optical path between the illumination assembly 101A and the detection unit 101B. For each location, tagged signal A or processed tagged signal A, is stored in memory, and the attenuation of the amplitude of the power spectrum of tagged signal A corresponding to the ultrasound frequency is determined.

In order to determine the absorption coefficient, following the determination of the reduced scattering coefficient at the above wavelengths, different wavelengths which are differently absorbed in the fluid (such as 1064 nm or 660 nm) are used and the above parameters are determined according to a specific method from those listed above. The absorption coefficient depends on the product of the concentration of the chromophores or structures within the fluid and the molar absorption coefficients (which are known in the literature). In order to determine the absorption coefficient, following the determination of the reduced scattering coefficient at the above wavelengths (735 nm and 780 nm), different wavelengths which are differently absorbed in the fluid (such as 1064 nm or 660 nm) are used to illuminate the body region. From the determined parameters of the signals at each wavelengths, the optical attenuation is obtained. The optical attenuation $\mu_{eff}$ is known to depend on both the reduced scattering ($\mu_{s'}$) and ($\mu_a$) absorption coefficients where $\mu_{eff} = \sqrt{3\mu_a(\mu_a+\mu_{s'})}$, since the reduced scattering coefficients were determined before, the absorption coefficients can be extracted.

Therefore, the concentration of absorbing centers (like meconium) is determined similar to the concentration of hemoglobin, as described above.

In some embodiments of the present invention, a threshold value for mature lungs is an input parameter to the control unit 120 prior to its operation. In some embodiments of the present invention, several parameters are being input into the control unit 120 prior to operation. Some parameters are measured by an ultrasound imager, such as, thickness of uterine wall or thickness of abdominal wall. Additional parameters may include weight of gravida and duration of gestation (relative to last menstrual period or based on other indicators). Some of these parameters are used to calculate the threshold value to which the optical properties of the amniotic fluid, or the concentration of lamellar bodies, are compared. These parameters can optionally be used to calculate the concentration of the lamellar bodies from the optical signals according to an algorithm that uses the optical properties of maternal tissues 11A to extract the optical attenuation in amniotic fluid 2A as explained above.

It should be noted that similar to the configuration of FIG. 2, illumination assembly 101A can be inserted transvaginally to illuminate a volume of amniotic fluid through the cervix. Choice of wavelengths for transcervical illumination may be different than choice of wavelengths for abdominal illumination, since the composition of the different tissue layers in between the illumination assembly 101A and the amniotic fluid 2A is different for the two configurations. For example, skin (epidermis) contains melanin that highly absorbs in the ultraviolet region, whereas the cervix has little or no melanin.

While it is preferred that the control unit 120 determines the concentration of lamellar bodies or meconium, it is not always necessary to determine these concentrations. A database of signals can be defined by recording signals collected by the controller's memory or features of these signals (e.g. amplitude, phase, frequency, time dependence, wavelets or principal components). The database may contain data from measurement obtained for premature fetal lungs and mature fetal lungs. For lung maturity classification by the database, a similarity metric is defined. The obtained signals are classified according to the best fit to mature or immature lungs using clustering, neural networks and/or other classification algorithms. For meconium stained analyses, the database can contain signals from stained and clear amniotic fluid. Features from the ultrasound image taken prior or during the assay are used to categorize the measured signals in the database.

Whereas the above examples relate to measuring the optical properties of amniotic fluid, similar apparatus can be designed for noninvasive measuring the optical properties of other extravascular fluids such as pleural (around the lungs), pericardial (around the heart), peritoneal (around the abdominal and pelvis cavities) and synovial (around the joints) fluids.

Figure 4:
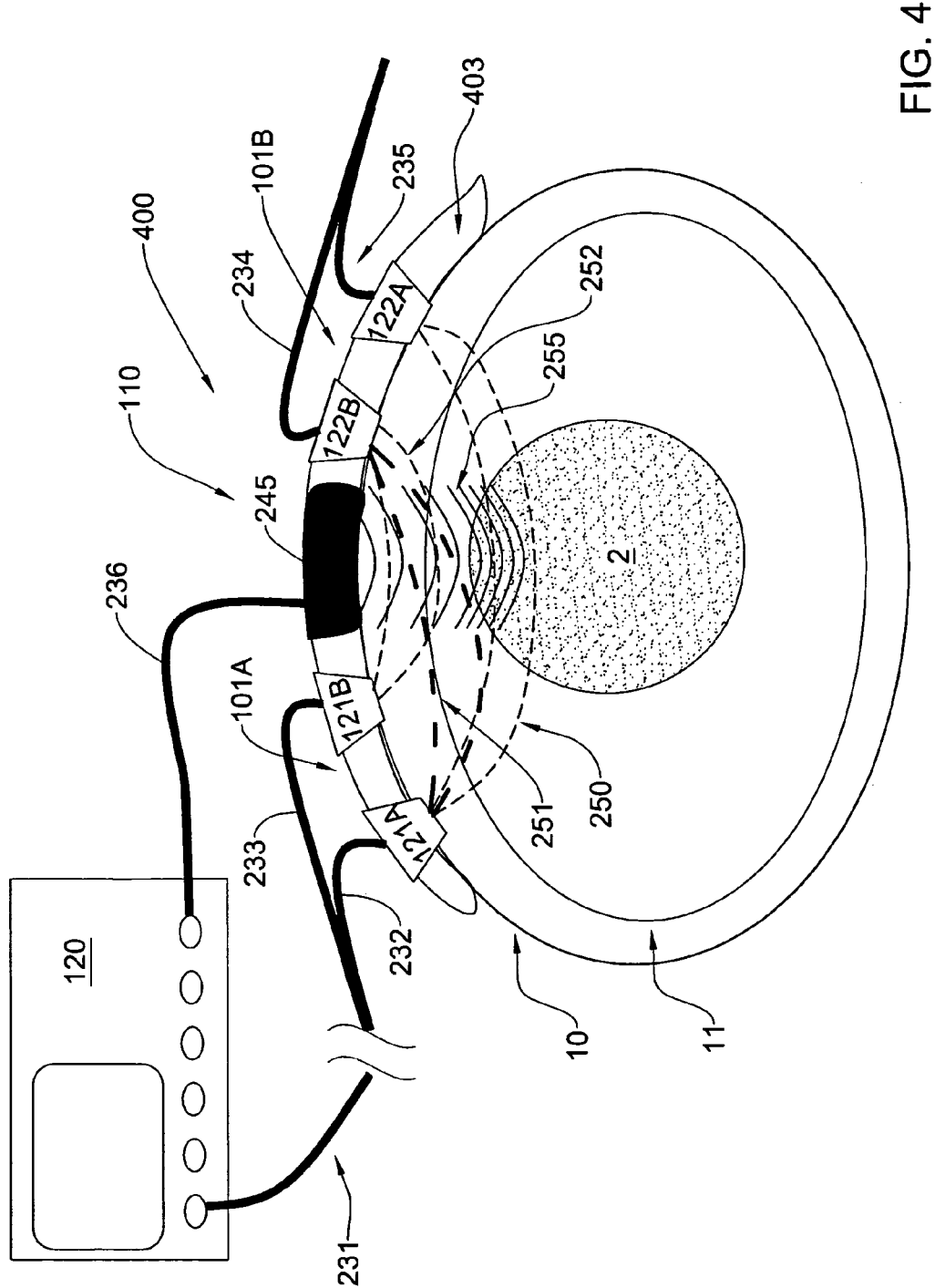
FIG. 4 schematically illustrates a monitoring apparatus, according to yet another embodiment of the present invention.

Reference is made to FIG. 4 exemplifying a monitoring apparatus 400 according to yet another embodiment of the invention. The apparatus is constructed and operable to enable determining properties of both maternal and fetal regions, for example detecting maternal and fetal oxygen saturation levels along with other tissue components. The apparatus 400 includes a measurement unit (optical and acoustic units) carried by a flexible probe 403; and is connectable to a control unit 120. The control unit 120 is similar to the above described control unit, namely is a computer system including inter alia a power supply, a control panel with input/output functions, a display unit, a function generator, electronic circuits, filters and processors, etc. Additionally, the control unit 120 may contain light sources, light detectors and acoustic sources. Electric wires, optical fibers and/or wireless means connect the control unit 120 to the elements of the measurement unit carried by the flexible probe 403. The flexible probe 403 includes light output ports 121A and 121B associated with an illumination assembly 101A, and light input ports 122A and 122B associated with a detection assembly 101B. It should be understood that the elements 121A and 121B carried by the probe 403 may be light sources (such as lasers, laser diodes or LEDs) or the output faces of optical fibers (or fiber bundles) whose input faces are coupled to light sources contained outside the probe, e.g., in the control unit 120. Similarly, elements 122A and 122B may be light detectors (such as for example diodes or CCD cameras) or the input faces of optical fibers or fiber bundles whose exit faces are coupled to light detectors located outside the probe, e.g., contained in the control unit 120. In the case actual detectors are placed on the flexible probe 403, the detectors are preferably mechanically and electronically isolated such that acoustic waves propagating from an acoustic output port 245 minimally affect the collection of photons by the detectors and the transduction of light signals into electronic signals. If the ultrasound transducer arrangement 110 is also placed on the probe 403, then the configuration is such as to prevent RF and other electronic signals generated by the transducer arrangement from interfering with the collection of photons by the detectors and with the transduction of light signals into electronic signals. Such a shielding of the detectors may for example include electrical isolation by appropriate materials that are poor conductors or create a Faraday cage around a detector, mechanical isolation by using appropriate material that attenuates the propagation of sheer acoustic waves through the probe itself or through maternal tissues. Detectors may be connected to the probe 403 using connecting parts (possibly detachable) that isolate mechanical and electrical signals at the frequencies generated by the ultrasound transducer arrangement and at other frequencies.

The detection assembly generates electronic signals in response to the amplitude and phase of photons reaching the input ports 122A and 122B. These electronic signals may be filtered by analog or digital filters, for example bandpass filters, that are appropriately provided being connected to the data processing utility of the control unit 120 or being a part of this processing utility. The bandwidth of these filters can be fixed or changed by the control unit 120. Tuning of the bandwidth can be performed optically by heterodyne detection or by a plurality of filters having different bandwidths, or by tunable filters which are coupled to each detector. Alternatively, filters can be electronic.

It should be noted that more than two input and output light ports may be provided in the monitoring apparatus 400, only two pairs of such ports being shown in the present example for the purposes of simplifying the illustration. In addition, each port may serve as a dual input and output light port by using a fiber combiner/splitter that couples light into and out of one optical fiber. The ports may be arranged in a one-dimensional array or a two-dimensional array to improve flexibility of use.

Preferably, the input and output ports are arranged such that an equal optical path through body tissues exists between pairs of output and input ports. For example, light input and output ports are arranged such that they are not coplanar, but rather form sets of isosceles triangles between output and input ports, having equal light paths between one output port and two input ports (or vice versa).

The flexible probe 403 also contains the ultrasound output port 245 from which acoustic waves 255 (shown as semicircles 255) are directed towards the region of interest. Acoustic waves 255 are generated by the ultrasound transducer arrangement 110 that may be located on the flexible probe 403 and connected to a function generator in the control unit 120 using electric wires 236 or using wireless means. Alternatively, the ultrasound transducer 110 may be located outside the probe 403, e.g., in the control unit 120, and acoustic waves be transmitted to the output port 245 using suitable acoustic waveguides 236. In the example of FIG. 4, the output port 245 is located between the light input and output ports.

The output port 245 may be placed at any location of the flexible probe 403 (i.e. to the right of output port 121A or the left of input port 122A). Several ultrasound output ports, at different locations along the flexible probe 403, may be used being coupled to the same ultrasound transducer arrangement or to different ultrasound transducer arrangements.

When different ultrasound transducer arrangements are used, the transducer arrangements may generate acoustic waves of the same frequency modulation, or each may generate a different frequency modulation. When different frequencies are being generated, the control unit 120 controls the modulation at each transducer arrangement according to the spatial locations of each output port associated with each transducer arrangement, such that light propagating through the same volume as the acoustic waves and collected through one or several light input ports is analyzed based on the correct frequency modulation of the corresponding transducer arrangement (as will be described below for one such transducer arrangement). Different transducer arrangements can generate acoustic waves at the same time intervals, or during different time intervals.

The flexible probe 403 is placed in contact with a maternal skin 10 in a region overlaying a fetal tissue 2 contained in maternal tissues. The positioning of the flexible probe 403 may be performed with the aid of an ultrasound imaging system that is used to determine the optimal location of light ports and acoustic output port relative to the fetus (as described above). Different fetal organs or tissues can be used to monitor fetal oxygen saturation including the placenta.

The flexible probe 403 is placed in contact with the maternal skin 10 using adhesive pads or by applying pressure to maternal abdomen using a belt. The acoustic output port 245 is coupled to the skin 10 using an acoustic coupling material such as gel or a hyrdrogel adhesive.

Upon attachment of the probe 403, the control unit 120 is turned on in a calibration mode. During the calibration mode, the control unit 120 sends an electronic signal to the function generator connected to the ultrasound transducer arrangement causing it to generate a series of acoustic pulses. The acoustic pulses are transmitted through the ultrasound output port 245 and propagate through maternal tissues 11 and fetal tissues 2. A portion of the acoustic pulses is reflected from each surface or impedance mismatched layer that the pulses encounter during their propagation. The reflected portion is collected through the acoustic output port 245 and transmitted to an ultrasound transducer of the imaging system (which may be the same transducer arrangement 110 used for measurements). The transducer arrangement used for imaging may be a single acoustic transmitter, a single acoustic transceiver, an array of transmitters and/or receivers, an ultrasound Doppler imager, a phased array, or a complete imaging system capable of transmitting and receiving acoustic signals. The control unit 120 analyzes the signals generated by the transducer in response to the portion of reflected pulses and determines a distance between the ultrasound output port 245 and the fetal tissues 2 (by multiplying the speed of sound in the tissue by half the time difference $\Delta\tau$ between the emission of the acoustic pulses from the output port 245 and the collection of the reflected pulses in the said port 245).

The control unit 120 then determines an appropriate distance to be provided between the light output port 121A or 121B and the light input port 122A or 122B, such that photons 250 emitted from the output port 121A will propagate through fetal tissues 2 before reaching the input port 122B. The control unit 120 can select which output and input ports are used from a plurality of light ports arranged at different spatial locations, such that at least one input port collects photons, emitted from at least one output port, that propagate through the same fetal tissue 2 through which acoustic waves 255 propagate. The control unit 120 also determines which of the other light input ports collect photons that propagate through maternal tissues 11 and not through fetal tissues 2. Additionally, during the calibration mode, the control unit 120 determines a desired frequency bandwidth $\Delta f_1$ that is to be used during the monitoring. For example, the control unit 120 selects the frequency bandwidth $\Delta f_1$ corresponding to that optimally filtered by analog or digital electronic filters connected to the light detectors.

Following the calibration mode, the control unit 120 operates an array of fixed output and input light ports by modulating (including time gating) the light sources connected only to the chosen output ports, or modulating the output ports themselves, and analyzing the signals generated by the detectors coupled to the chosen input ports.

As indicated above, the control unit 120 determines the desired frequency bandwidth $\Delta f_1$ to be used during the monitoring as that corresponding to a frequency bandwidth optimally filtered by analog or digital electronic filters connected to the light detectors. The bandwidth that these filters optimally transmit is fixed or varied by the control unit 120 during the operation of the apparatus 400. The control unit 120 controls a portion of the frequency bandwidth generated by the function generator to correspond to the frequency bandwidth that is optimally transmittable by the electronic filters connected to the light detectors. Alternatively, the bandwidth of the filters is varied by the control unit 120 to correspond to a portion of the frequency bandwidth generated by the function generator. The control unit 120 also controls the frequency modulation of acoustic waves 255 such that waves having a frequency outside the frequency bandwidth $\Delta f_1$ are for example generated during different portions of the acoustic pulse.

The control unit 120 controls the time dependent generation of the frequency modulated acoustic waves. The control unit 120 determines a time period $\Delta t_1$ needed for signal acquisition such that optimal signal-to-noise ratio (SNR) for determining fetal oxygen saturation is obtained during the measurements. The time period $\Delta t_1$ is shorter than a time difference between the fetal heart beats, when pulse oximetry is used for data analysis. The control unit 120 also determines the frequency modulation parameters such that the desired frequency bandwidth $\Delta f_1$, (or phase) propagates through the fetal tissue 2 during the time period $\Delta t_1$. The onset of time period is at time $t_1$ equal to about $\Delta\tau/2$ where the acoustic pulse reaches the fetal tissues 2 and time $t_2$ is determined by $t_2 = t_1 + \Delta t_1$.

In the present example of FIG. 4, the operation of apparatus 400 in a "monitor mode" or actual measurement mode is shown. During the monitor mode, the control unit 120 activates the light source(s) associated with the output port 121A to emit photons 250 and 251, and actuates the light source(s) associated with the output port 121B to emit photons 252. The light ports may be associated with different light sources or with one or more common light sources. A single light source and preferably two light sources, emitting light of at least two different wavelengths simultaneously, are connected to the output ports, whereas one light source may be connected to more than one output port. Light sources connected to different output ports, or output ports themselves, may be activated during different time periods or with different characteristics (such as different modulation frequency or phase), such that the control unit 120 can distinguish between photons 251 and 252 reaching input port 122B of the detection unit.

The control unit 120 also activates a function generator that, in turn, activates the ultrasound transducer arrangement 110 to generate acoustic waves 255 transmitted through the output port 245. The acoustic wave frequency (or phase) generated by the function generator is modulated by the control unit 120 such that the acoustic waves reaching a region of the fetal tissue 2 illuminated by photons 250 will have a predetermined frequency bandwidth $\Delta f_1$. If the bandwidth $\Delta f_1$ is fixed, then the control unit 120 determines the frequency modulation of the function generator controlling the generation of ultrasound waves 255, such that acoustic waves 255 modulated at a frequency within $\Delta f_1$ reach the fetal tissues 2 at time $t_1$. In addition, acoustic waves with a frequency within $\Delta f_1$ substantially do not propagate through other tissues during the time period $\Delta t_1$ following time $t_1$. Accordingly, the control unit operates the detection assembly such that the light detectors associated with the input ports 122A and 122B start collection of photons at time $t_1$ and end the collection process during $t_2$. Alternatively or additionally, the control unit 120 controls the activation of light sources associated with the output ports 121A and/or 121B at time $t_1$ and ends the activation at time $t_2$. During the time period $\Delta t_1$, the input port 122A and/or input port 122B collect photons propagating through the same fetal tissues through which acoustic waves 255 propagate (a time delay in photon propagation through the tissue is neglected).

Figure 5:
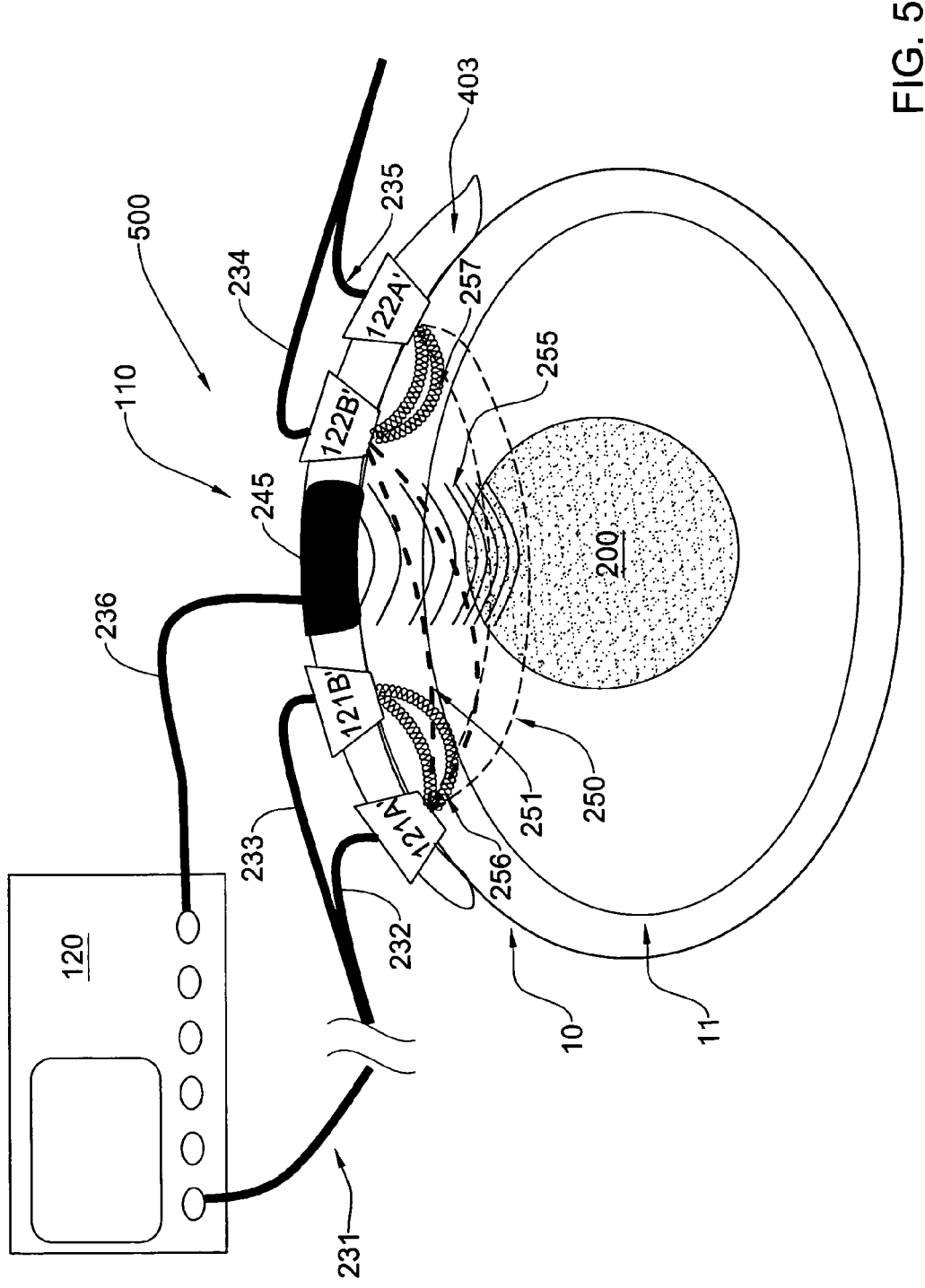
FIG. 5 schematically illustrates a monitoring apparatus, according to yet another embodiment of the present invention.

FIG. 5 exemplifies a monitoring apparatus 500 of a somewhat different configuration. Apparatus 500 differs from the above-described apparatus 400 in the arrangement of input and output ports (or light sources and detectors) within a flexible probe 403. Here, light port 121A' functions as an output port (associated with the illumination assembly), light ports 121B' and 122A' function as both output and input ports (associated with the illumination assembly and detection unit), and light port 122B' functions as an input port (associated with the detection unit).

In addition, all input ports may be time gated to collect light propagating through specific tissues during a certain time period. Additionally or alternatively, the output ports may be activated during different time intervals. For example, the input ports 121B' or 122B' are activated during a time interval $\Delta t_g$, following the introduction of light from the output ports 121A' or 122A', respectively, such that only photons 256 propagating from the output port 121A' to the input port 121B' or photons 257 propagating from the output port 122A' to the input port 122B' are collected during that time interval. The output ports 121A' and 122A' are therefore activated at different time intervals, such that the input port 122B' does not collect photons 251 and 257 simultaneously. During a time interval $\Delta t_k$, different from $\Delta t_g$, the input port 122A' is activated, following the introduction of light from the output ports 121A', such that only photons 250 propagating through fetal tissues 2, are detected. As will be explained below, during the time interval $\Delta t_g$ the light input ports collect light propagating primarily through maternal tissues, being untagged. During time interval $\Delta t_g$ acoustic waves 255 do not propagate through the same volume from which light is collected by the input ports 121B' and 122B'. During time interval $\Delta t_k$ the light input ports collect light propagating primarily through maternal and fetal tissues, being tagged or untagged.

It is preferred that the time interval $\Delta t_k$ corresponds to the time interval $\Delta t_1$ defined above, where both intervals start at $t_1$. It is preferred that the intervals $\Delta t_k$ and $\Delta t_g$ are closely spaced in time such that no substantial modulation in blood or tissue characteristics occurs in between these time intervals.

Alternatively, several light input ports may be activated during different time intervals corresponding to light propagation through either maternal tissues alone or maternal and fetal tissues, and different acoustic waves can optionally propagate through all volumes from which light is collected allowing both tagged and untagged light to be analyzed through every input port.

Tagged and untagged signals collected by all the input ports are used to determine the fetal oxygen saturation level based on the tissue models A and B described above. The amplitudes of the tagged and untagged signals are determined during the time intervals $\Delta t_k$ and $\Delta t_g$ respectively.

The filtered electronic signal at a selected bandwidth $\Delta f_1$, during the time period $\Delta t_1$, starting at $t_1$, corresponds to the amplitude of the tagged signal propagating through the fetal tissue 2. Photons 250 propagating through other tissue regions, during the time period $\Delta t_1$, where the frequency of the ultrasound waves 255 is outside the frequency bandwidth $\Delta f_1$, will have a different modulation frequency and will be attenuated by the filters having the bandwidth of $\Delta f_1$. The electronic filters connected to the light detectors can have several bandwidths of optimal transmission ($\Delta f_2 \ldots \Delta f_n$) different from $\Delta f_1$. Detectors are configured such that during each time period $\Delta t_i$ (i=1 ... n) starting at time $t_i$, where $t_i$ is the time where portion of acoustic pulse having a frequency modulation with a bandwidth $\Delta f_i$ reaches the fetal tissue 2, the detectors are tuned to optimally convert photons, modulated by frequency $\Delta f_i$, to electrical signals.

For example, as the modulated ultrasound waves propagate through maternal and fetal tissues, at different time periods ($\Delta t_2 \ldots \Delta t_n$) different from $\Delta t_1$, acoustic waves at different frequency modulations propagate through the fetal tissues. The control unit 120 then operates each filter according to the order and duration of the different frequency modulations within the ultrasound pulse, such that each electronic filter having a frequency bandwidth $\Delta f_i$ is activated at time periods $\Delta t_i$ starting at $t_i$ in accordance with the corresponding frequency bandwidth of the ultrasound wave. Additionally, the electronic filter can have a variable bandwidth that is controlled by the control unit 120 in accordance with the generation of the frequency modulation of the ultrasound wave. The control unit 120 then integrates the electronic signals generated by the light detectors and filtered by the electronic filters at all frequency bandwidths during the corresponding time periods. The control unit 120 then analyzes signals received from the electronic filters to determine the fetal and/or maternal oxygen saturation levels.

Referring to either one to FIGS. 4 and 5, the control unit 120 analyzes tagged signals, reaching at least one of the input ports of the detection units and being modulated at frequency bandwidth $\Delta f_m$ different from $\Delta f_i$ (i=1 ... n), during a time period $\Delta t_i$ starting at $t_i$, to determine the properties of maternal tissues through which photons 251 and/or 252 (in FIG. 4) propagate. These signals may optionally be used to determine maternal oxygen saturation levels. The control unit 120 then uses the tagged signals having a modulation corresponding to frequency bandwidth $\Delta f_m$ in model B described above to determine characteristics of maternal tissues. The control unit 120 then calibrates model A as described above. The control unit 120 then uses tagged signals, reaching the input ports of the detection units and being modulated at the frequency bandwidth corresponding to $\Delta f_1$ during the same time period $\Delta t_i$ starting at $t_i$ in accordance with model A to determine fetal oxygen saturation levels.

It should be noted with respect to the above-described examples, that the transducer arrangement 110 may include an ultrasound imaging system and/or and ultrasound Doppler imager, such that ultrasound images or Doppler signals are acquired during operation of the monitoring apparatus. Prior to and during the operation, an ultrasound image of tissues including the region of interest is first acquired. The control unit 120 (or the operator) identifies the region of interest by marking this region on the first acquired ultrasound image. Transducer arrangement 110 is then fixed at the same location (by the operator or by using an adhesive), for duration necessary to obtain efficient tagged signals from the region of interest. The control unit 120 determines the corresponding distance, angle and size of the region of interest relative to the transducer arrangement 110. Then, the control unit 120 operates to select input and output light ports to emit light and collect light propagating through the region of interest and the outside region, as described above (i.e., to ensure optimal positioning during the measurements). The control unit 120 synchronizes the activation of the light output ports and/or light input ports such that emission of ultrasound pulses to the region of interest corresponds to the propagation of light pulses through the region of interest. Alternatively, the control unit 120 synchronizes the emission of acoustic pulses by the transducer arrangement 110 such that the onset, duration and direction of these pulses correspond to the onset and duration of the activation of light input and/or output ports. The control unit 120 analyzes tagged and untagged signals generated by the detection assembly and determines the concentration of an analyte (for example, oxygenated hemoglobin) in the region of interest, as described above. More than one analyte can be monitored simultaneously by using different wavelengths of light, each having a characteristic absorption or scattering by the selected analytes. The control unit 120 then displays simultaneously (using, for example, color coded images) the local concentration of the analyte on the region of interest of the ultrasound image, in addition to any other form of display (e.g. numerical) that is understood by the operator and/or by a machine connected to the control unit 120. In cases where more than one ultrasound pulse is needed for obtaining efficient tagged light signals, the transducer arrangement is operated without scanning the ultrasound beam, and a single beam is emitted in the direction of the region of interest for the duration needed for an efficient tagged signal acquisition. Yet another option suitable for cases when the transducer arrangement is moved during operation, such that distances and angles between the transducer arrangement 110 and the region of interest are changed, the control unit 120 tracks the position of the region of interest using techniques and algorithms such as of three-dimensional ultrasound imaging (F. Rousseau, P. Hellier, C. Barillot, "Calibration Method for 3D Freehand Ultrasound", In Medical Image Computing and Computer Assisted Intervention, MICCAI'03, Montreal, Canada, November 2003). The control unit 120 then determines the changed distance and angle to the region of interest, and dynamically selects and activates corresponding input and output light ports accordingly during the movement of the transducer arrangement 110.

In another embodiment of the invention, an imaging apparatus may be used to monitor changes in the concentration of analyte(s) in a region of interest during therapeutic or surgical procedures (such as during the application of high power ultrasound pulses or wave, laser ablation, or chemical procedures). For example, the transducer arrangement 110 may be used for ablation of tumors or malformations in a tissue. During the application of high power ultrasound pulses, light is emitted and collected by illumination and detection assemblies, respectively, to determine the concentration of an analyte indicative of the treatment in the region being ablated. Alternatively, low power ultrasound pulses (that do not cause ablation) intermittently irradiate the region of interest, while low-power light pulses are emitted and collected by illumination and detection assemblies to determine the concentration of an analyte indicative of the treatment. For example, oxygenation of the region of interest is monitored. Such information is used for controlling and monitoring the treatment during application of ultrasound radiation.

Figure 6A:
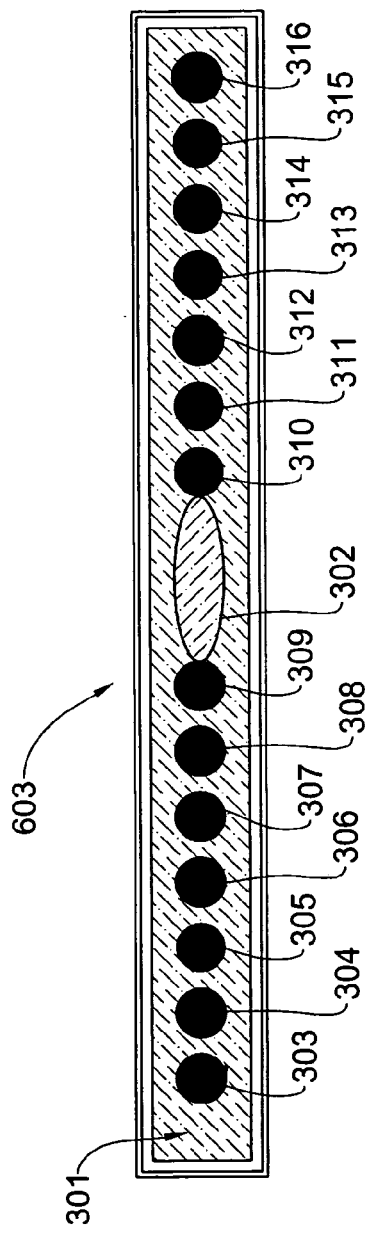
FIGS. 6A and 6B show bottom and side views, respectively, of a flexible probe according to one embodiment of the invention.
Figure 6B:
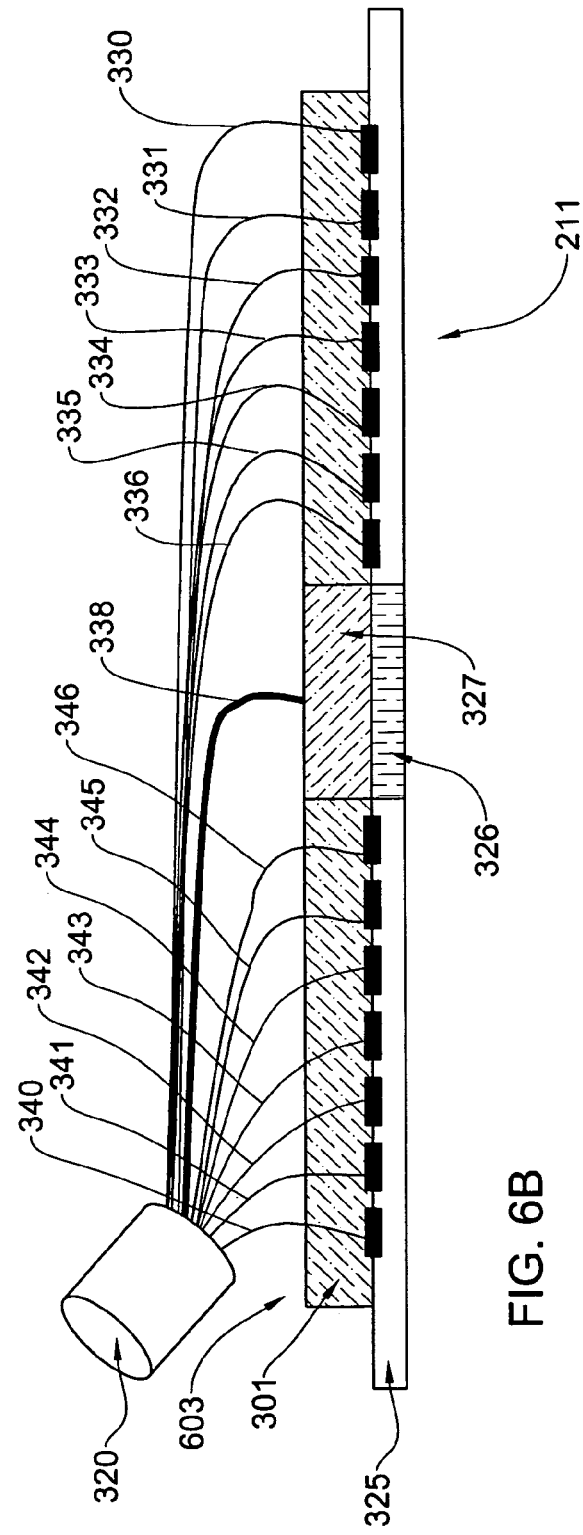

Reference is now made to FIGS. 6A and 6B exemplify yet another configuration of a flexible probe, generally designated 603, suitable to be used in either one of the above described monitoring apparatuses. The flexible probe 603 includes a flexible support 301, for example made of electrically isolating material(s), carrying light ports 303-316 (fiber-ends in appropriate housing, or light sources and/or light detectors as described above) and an acoustic output port 302 (or acoustic transducer arrangement). FIG. 6A presents a bottom view of the flexible probe 603 viewed from the side by which it is attachable to a skin, and FIG. 6B shows a side view diagram of the flexible probe 603. Optical fibers or electric wires 330-336 and 340-346 connect the light ports 310-316 and 303-309, respectively, to a common connector 320. An isolated electric cable (or acoustic waveguides) connects the acoustic output port 302 to the same connector 320 associated with a control unit. The acoustic port 302 is preferably coupled to an ultrasound transducer arrangement 327 connected to the flexible support 301 using vibration controlling elements. The connector 320 couples the optical fibers and cables attached to the flexible support 301 with optical fibers and electric cables coupled to the control unit (not shown here). The connector 320 may be composed of several connector elements. An adhesive 325 is attached to the bottom side of the support 301, such that the probe 603 can be fixed to the skin using this adhesive 325. Adhesive 325 is preferably transparent and produces minimal scattering in a wavelength range used for measurements (i.e., emitted by light sources). Alternatively or additionally, the adhesive 325 may form an optical index matching layer between the light ports and the skin. Alternatively, the adhesive 325 may not cover the light ports at all, or may partially cover them. The adhesive 325 may contain pigments, chromophores or other materials for controlling the transmission of different wavelengths of light. An adhesive gel 326 is located below the acoustic port 302. The adhesive gel 326 is made from the same or different material as the adhesive 325 and is designed for optimal acoustic coupling between the acoustic port 302 and the skin. Possible materials for adhesives 325 and 326 include hydrogel based adhesives.

The different elements of the flexible probe 603 may be assembled in different ways. For example, the complete probe 603 is assembled prior to operation, and a user only needs to remove a thin layer covering the bottom side of adhesives 325 and 326. In yet another example, the adhesive 326 is attached to the acoustic output port 302 (preferably including the acoustic transducer arrangement itself) which is not attached to the probe 603 prior to the device operation. The user first attaches the flexible support 301 to the skin using the adhesive 325, and then inserts the acoustic port 302 through an appropriately provided opening in the support 301, where the transducer 327 is optionally connected to the support 301 using conventional means and is attached to the skin using the adhesive 326. The latter may be part of adhesive 325, and only the acoustic output port 302 is inserted and attached to the upper part of the adhesive 326 (being a double sided adhesive). The user first attaches the adhesives 325 and 326 to skin, then attaches the acoustic port 302 to the adhesive 326, and then connects the support 301 to the upper side of the adhesive 325 (being a double sided adhesive). Finally, the connector 320 is connected to the cables and fibers from the control unit to allow the operation of the probe. Each element of the flexible probe 603 and the complete probe 603 as a unit may be used only once and then discarded (i.e., is disposable), or used multiple times.

Figure 7A:
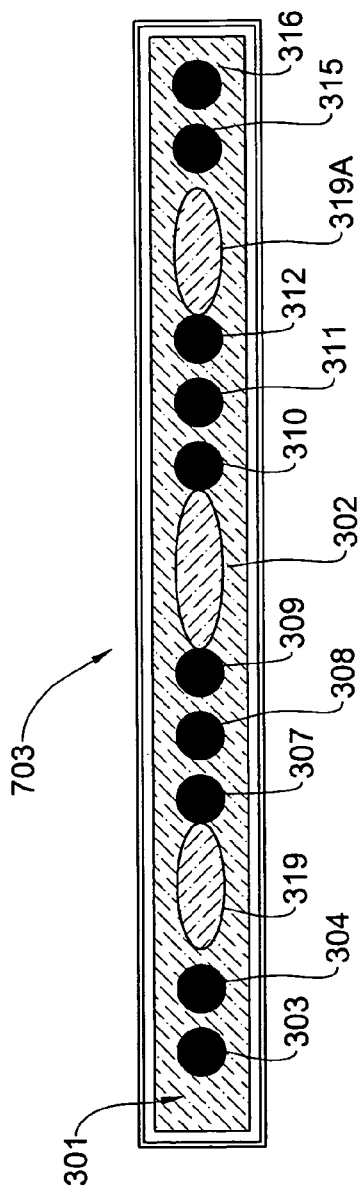
FIGS. 7A and 7B show bottom and side views, respectively, of a flexible probe according to another embodiment of the invention.
Figure 7B:
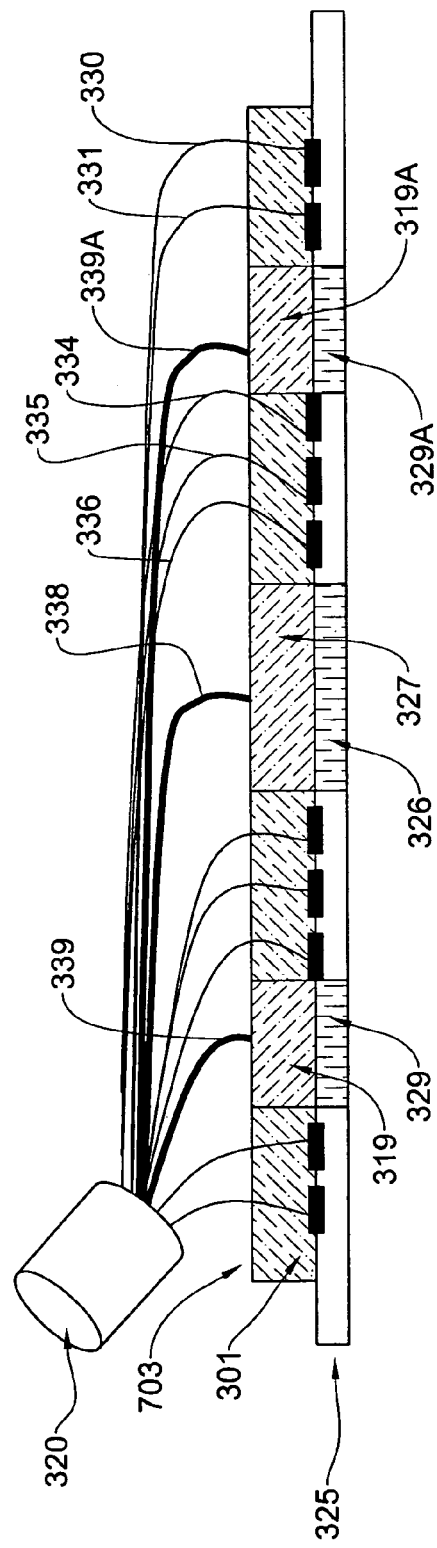

FIGS. 7A and 7B show yet another example of a flexible probe 703 according to the present invention. Here, a support 301 carries light ports (or light sources) and several acoustic ports 302, 319 and 319A (or acoustic transducer arrangements). Each of the acoustic ports 302, 319 and 319A is coupled to a connector 320 using cables 338, 339 and 339A, respectively. Adhesive gels 326, 329 and 329A are used to couple the acoustic ports 302, 319 and 319A, respectively, to the skin. Similarly, each of the acoustic ports may be separated from the probe 703 when not in use, and inserted by user for as preparation for operation.

Those skilled in the art will readily appreciate that various modifications and changes may be applied to the embodiments of the invention as hereinbefore described without departing from its scope defined in and by the appended claims.

The invention claimed is:

1. A probe device for use in a system for monitoring at least one parameter of a region of interest in a human body, the probe device comprising:
a support structure carrying an arrangement of one or more light output ports of a light source assembly, one or more light input ports of a light detection assembly, and at least one acoustic output port of an acoustic unit,
the arrangement of the light and acoustic ports within the support structure facilitating placement of the at least light output port, the at least one light input port, and the at least one acoustic output port with respect to the body, such that at least one operative light output port, at least one operative light input port, and at least one operative acoustic output port are selectable, so as to provide an operating condition, at which
acoustic waves of a predetermined frequency range coming from said at least one selected acoustic output port and illuminating light coming from said at least one selected light output port overlap in a region within the region of interest in the body, thereby inducing tagging of light by said acoustic waves,
the acoustic waves substantially do not overlap with illuminating light coming from said at least one selected light output port in a region outside the region of interest, the light outside the region of interest thereby substantially not being tagged by said acoustic waves, and
said at least one selected light input port collects tagged light scattered from the overlapping region and substantially untagged light scattered from outside the region of interest; and
a control unit configured to select the at least one operative light output port, the at least one operative light input port, and the at least one operative acoustic output port, so as to provide the operating condition.

2. The probe of claim 1, wherein the support structure is configured such that the arrangement of the light and acoustic ports is such that the light input and output ports are orientable with respect to one another such that the collection of the light by the at least one selected light input port includes the light scattered from the overlapping region, and the light scattered from outside the region of interest the collection of the light from the overlapping region and the light from outside the region of interest enabling identification of a light response of the region of interest.

3. The probe device of claim 1, wherein the support structure is configured such that the arrangement of the light and acoustic ports is configured to provide said condition for the probe operation such that the acoustic waves of the predetermined frequency range from said at least one selected acoustic port and the scattered light, that is irradiated from the at least one selected light output port and is collected by the at least one operative light input port, overlap within the region of interest in the body simultaneously.

4. The probe device of claim 1, wherein the support structure is configured such that said arrangement of light input and acoustic ports within the support structure is adapted to enable selection of one of the light input ports, one of the light output ports, and at least one of the acoustic ports to provide the operating condition.

5. The probe device of claim 1, wherein the support structure is configured such that said arrangement of light input and acoustic ports within the support structure is adapted to enable selection of at least two of the light output ports, at least one of the light input ports, and at least one of the acoustic output ports to provide the operating condition.

6. The probe device of claim 1, wherein the light input ports comprise at least two light input ports arranged in a spaced-apart relationship, and wherein the support structure is configured such that said arrangement of light input and acoustic ports within the support structure is adapted to enable selection of at least one of the light output ports, at least the two light input ports, and at least one of the acoustic output ports to provide the operating condition.

7. The probe device of claim 1, wherein the light input ports comprise an array of at least two light input ports arranged in a spaced-apart relationship, wherein the light output ports comprise an array of at least two light output ports arranged in a spaced-apart relationship, and wherein said arrangement of light input and acoustic ports within the support structure is adapted to enable selection of the array of at least two light output ports, the array of light input ports, and at least one of the acoustic output ports to provide the operating condition.

8. The probe device of claim 1, wherein the acoustic port is configured to provide the acoustic radiation substantially non-collinear with a line connecting the selected operative light input and output ports.

9. The probe device of claim 1, wherein the support structure is configured such that the arrangement of the light and acoustic ports is configured and operable to provide a relative displacement between a direction of propagation of the acoustic radiation and at least one of the light input and output ports.

10. The probe device of claim 1, wherein the support structure carries the light source assembly.

11. The probe device of claim 10, wherein the support structure carries the light detection assembly.

12. The probe device of claim 11, wherein the support structure carries the acoustic unit.

13. The probe device of claim 10, wherein the support structure carries the acoustic unit.

14. The probe device of claim 1, wherein the support structure carries the light detection assembly.

15. The probe device of claim 14, wherein the support structure carries the acoustic unit.

16. The probe device of claim 1, wherein the support structure carries the acoustic unit.

17. The probe device of claim 1, wherein the support structure is flexible such that the support structure is configured to be wrapped around a body portion of the subject that contains the region of interest.

18. The probe device of claim 1, wherein the acoustic unit is configured and operable for generating a type of ultrasound radiation selected from the group consisting of: continuous wave radiation, pulse radiation, and burst radiation.

19. The probe device of claim 1, wherein the acoustic unit is configured and operable for carrying out a technique selected from the group consisting of: generating unfocused ultrasound radiation; and generating focused ultrasound radiation with a focal length corresponding to a distance from the acoustic unit to the region of interest.

20. The probe device of claim 1, wherein the acoustic unit has a configuration selected from the group consisting of: a configuration in which the acoustic unit comprises a phased array of ultrasound transducers; a configuration in which the acoustic unit comprises a single-element ultrasound transducer; a configuration in which the acoustic unit comprises an imaging ultrasound probe; and a configuration in which the acoustic unit comprises Doppler imaging elements.

21. The probe device of claim 1, wherein the control unit is configured and operable to:
generate measured data indicative of variations of the ultrasound tagged light signal as a function of at least one of time and wavelength of the illuminating light,
analyze the variations of the ultrasound tagged light signal, and
determine at least one predetermined characteristic of the signal and calculate oxygen saturation of the region of interest, said at least one predetermined characteristic including at least one of maxima, minima, and average of the signal.

22. The probe device of claim 1, wherein the light source assembly is configured and operable to carry out at least one technique selected from the group consisting of: (a) generating the illuminating light of at least two different wavelengths; (b) generating the illuminating light of at least two different wavelengths at different times; (c) generating the illuminating light of at least two wavelengths differently modulated by at least one of frequency and phase characteristics.

23. The probe device of claim 22, wherein the light source assembly is configured and operable to generate the illuminating light of at least three different wavelengths,
of which two of the wavelengths are characterized, with respect to one another, by having the same absorption by tissue or fluid components in the body and as being differently scattered by the tissue or fluid components in the body, and
of which two of the wavelengths are characterized, with respect to one another, by having different absorption by the tissue or fluid components in the body.

24. The probe device of claim 1, wherein the detection assembly has a configuration selected from the group consisting of:
(i) a configuration in which the detection assembly defines the light input port such that, when in the operating condition of the probe, the light input port detects both the light scattered from the region of interest and the light scattered from the outside of the region of interest;
(ii) a configuration in which the detection assembly defines at least two spaced-apart light input ports, such that in the operating condition at least one of the light input ports collects the tagged light coming from the region of interest, and at least one other of the light input ports collects the untagged light scattered from the region outside the region of interest.

25. The probe device of claim 1, wherein the arrangement of light and acoustic ports is configured such that at least one of the light input ports is located proximate of the light output port thereby collecting untagged light scattered from the region outside of the region of interest; and the at least one other light input port is located at a larger distance from the light output port thereby collecting ultrasound tagged light coming from the region of interest through the outside region.

26. The probe device of claim 1, wherein the acoustic unit is configured and operable to generate ultrasound radiation with a frequency range of about 50 kHz-8 MHz.

27. A probe device for use in a system for monitoring at least one parameter of a region of interest in a human body, the probe device comprising:
a support structure carrying:
an array of at least two light output ports arranged in a spaced-apart relationship and being optically coupled to a light source assembly,
an array of light input ports arranged in a spaced-apart relationship and being optically coupled to a light detection assembly, and
at least one acoustic output port of an acoustic unit,
the arrangement of the light ports and the acoustic unit being such as to allow selection of at least one of said light output ports, at least one of the light input ports and at least one of the acoustic output ports, such as to provide an operating condition in which:
acoustic waves of a predetermined frequency range coming from said at least one selected acoustic output port and illuminating light coming from said at least one selected light output port overlap within a region of interest in the body, thereby inducing tagging of light by said acoustic waves,
the acoustic waves substantially do not overlap with illuminating light coming from said at least one selected light output port in a region outside the region of interest, the light outside the region of interest thereby substantially not being tagged by said acoustic waves, the light outside the region of interest thereby substantially not being tagged by said acoustic waves, and
at least one light input port collects tagged light scattered from the overlapping region and substantially untagged light scattered from outside the region of interest; and
a control unit configured to select the at least one of said light output ports, at least one of the light input ports, and at least one of the acoustic output ports, so as to provide the operating condition.

28. A probe device for use in a system for monitoring at least one parameter of a region of interest in a human body, the probe device comprising:
a support structure carrying at least one light output port optically coupled to a light source assembly, at least two light input ports optically coupled to a light detection assembly, and at least one acoustic output port of an acoustic unit,
the arrangement of the light and acoustic ports being such as to allow selection of at least one of the light input ports and at least one of the acoustic output ports, such as to provide an operating condition in which:
acoustic waves of a predetermined frequency range coming from said at least one selected acoustic output port and illuminating light coming from said at least one selected light output port overlap within a region of interest in the body, thereby inducing tagging of light by said acoustic waves, the acoustic waves substantially do not overlap with illuminating light coming from said at least one selected light output port in a region outside the region of interest, the light outside the region of interest thereby substantially not being tagged by said acoustic waves, the light outside the region of interest thereby substantially not being tagged by said acoustic waves, and said at least one light input port collects tagged light scattered from the overlapping region and substantially untagged light scattered from outside the region of interest; and a control unit configured to select the at least one of the light input ports and at least one of the acoustic output ports, so as to provide the operating condition.

29. A probe device for use in a system for monitoring at least one parameter of a region of interest in a human body, the probe device comprising:

a support structure carrying at least two light output port optically coupled to a light source assembly, at least one light input port optically coupled to a light detection assembly, and at least one acoustic output port of an acoustic unit, the arrangement of the light and acoustic ports being such as to allow selection of at least one of said light output ports, at least one of the light input ports and at least one of the acoustic output ports, such as to provide an operating condition in which:

acoustic waves of a predetermined frequency range coming from said at least one selected acoustic output port and illuminating light coming from said at least one selected light output port overlap within a region of interest in the body, thereby inducing tagging of light by said acoustic waves, the acoustic waves substantially do not overlap with illuminating light coming from said at least one selected light output port in a region outside the region of interest, the light outside the region of interest thereby substantially not being tagged by said acoustic waves, the light outside the region of interest thereby substantially not being tagged by said acoustic waves, and said at least one light input port collects tagged light scattered from the overlapping region and substantially untagged light scattered from outside the region of interest; and a control unit configured to select the at least one of said light output ports, at least one of the light input ports and at least one of the acoustic output ports, so as to provide the operating condition.

30. A probe device for use in a system for monitoring at least one parameter of a region of interest in a human body, the probe device comprising:

a support structure having a configuration selected from the group consisting of:

(i) a configuration in which the support structure carries at least two light output port optically coupled to a light source assembly, at least one light input port optically coupled to a light detection assembly, and at least one acoustic output port of an acoustic unit, (ii) a configuration in which the support structure carries at least one light output port optically coupled to a light source assembly, at least two light input ports optically coupled to a light detection assembly, and at least one acoustic output port of an acoustic unit, and (iii) a configuration in which the support structure carries an array of at least two light output ports arranged in a spaced-apart relationship and being optically coupled to a light source assembly, an array of light input ports arranged in a spaced-apart relationship and being optically coupled to a light detection assembly, and at least one acoustic output port of an acoustic unit, the arrangement of the light and acoustic ports being such as to allow selection of at least one of said light output ports, at least one of said light input ports and at least one of the acoustic output ports such as to provide an operating condition in which:

acoustic waves of a predetermined frequency range coming from said at least one selected acoustic output port and illuminating light coming from said at least one selected light output port overlap within a region of interest in the body, thereby inducing tagging of light by said acoustic waves, the acoustic waves substantially do not overlap with illuminating light coming from said at least one selected light output port in a region outside the region of interest, the light outside the region of interest thereby substantially not being tagged by said acoustic waves, the light outside the region of interest thereby substantially not being tagged by said acoustic waves, and said at least one light input port collects tagged light scattered from the overlapping region and substantially untagged light scattered from outside the region of interest; and a control unit configured to select the at least one of said light output ports, at least one of said light input ports and at least one of the acoustic output ports, so as to provide the operating condition.

* * * * *